(12) United States Patent
Drown et al.

(10) Patent No.: US 11,896,288 B2
(45) Date of Patent: Feb. 13, 2024

(54) METHOD AND APPARATUS FOR MAGNETIC RESONANCE IMAGING THERMOMETRY

(71) Applicant: Medtronic Navigation, Inc., Louisville, CO (US)

(72) Inventors: Christine R. Drown, Westminster, CO (US); Andrew Wald, Denver, CO (US); Rebecca L. Vincelette, Arvada, CO (US); William A. Grissom, Nashville, TN (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 17/879,823

(22) Filed: Aug. 3, 2022

(65) Prior Publication Data

US 2022/0378493 A1  Dec. 1, 2022

Related U.S. Application Data

(63) Continuation of application No. 16/282,213, filed on Feb. 21, 2019, now Pat. No. 11,426,229.

(51) Int. Cl.
| | |
|---|---|
| *A61B 90/00* | (2016.01) |
| *A61B 18/14* | (2006.01) |
| *A61B 5/01* | (2006.01) |
| *A61B 5/055* | (2006.01) |
| *A61B 18/20* | (2006.01) |

(Continued)

(52) U.S. Cl.
CPC ............... *A61B 18/14* (2013.01); *A61B 5/01* (2013.01); *A61B 5/055* (2013.01); *A61B 18/20* (2013.01); *A61B 90/37* (2016.02); *G01R 33/4808* (2013.01); *A61B 18/02* (2013.01); *A61B 2018/00446* (2013.01); *A61B 2018/00577* (2013.01); *A61B 2018/00791* (2013.01); *A61B 2090/374* (2016.02); *A61B 2090/376* (2016.02); *G01R 33/4804* (2013.01)

(58) Field of Classification Search
CPC ........... A61B 5/01; A61B 5/055; A61B 90/37; A61B 2018/00791; G01R 33/4808
See application file for complete search history.

(56) References Cited

U.S. PATENT DOCUMENTS

| | | | |
|---|---|---|---|
| 5,592,939 A | 1/1997 | Martinelli | |
| 5,835,620 A * | 11/1998 | Kaplan | G06V 10/24 382/128 |

(Continued)

FOREIGN PATENT DOCUMENTS

| | | |
|---|---|---|
| EP | 0472806 A2 | 3/1992 |
| EP | 2033567 A1 | 3/2009 |

(Continued)

OTHER PUBLICATIONS

U.S. Appl. No. 16/282,193, 2020-0273175, filed Feb. 21, 2019, Christine R. Drown et al.

(Continued)

*Primary Examiner* — Jason M Ip
(74) *Attorney, Agent, or Firm* — Harness, Dickey & Pierce, P.L.C.

(57) ABSTRACT

A system and method to analyze image data. The image data may be used to assist in determine the presence of a feature in the image. The feature may include a bubble.

17 Claims, 12 Drawing Sheets

(51) Int. Cl.
    *G01R 33/48* (2006.01)
    *A61B 18/02* (2006.01)
    *A61B 18/00* (2006.01)

(56) References Cited

U.S. PATENT DOCUMENTS

| | | | |
|---|---|---|---|
| 5,913,820 | A | 6/1999 | Bladen et al. |
| 6,067,371 | A | 5/2000 | Gouge et al. |
| 6,119,033 | A | 9/2000 | Spigelman et al. |
| 6,228,028 | B1 | 5/2001 | Klein et al. |
| 6,326,786 | B1 | 12/2001 | Pruessmann et al. |
| 6,381,485 | B1 | 4/2002 | Hunter et al. |
| 6,474,341 | B1 | 11/2002 | Hunter et al. |
| 7,227,359 | B2 | 6/2007 | Ma |
| 7,270,656 | B2 | 9/2007 | Gowda et al. |
| 7,570,791 | B2 | 8/2009 | Frank et al. |
| 7,751,865 | B2 | 7/2010 | Jascob et al. |
| RE42,226 | E | 3/2011 | Foley et al. |
| 8,340,376 | B2 | 12/2012 | Simon |
| 9,002,022 | B1 | 4/2015 | Clemen, Jr. |
| 9,743,909 | B1 | 8/2017 | Sapozhnikov et al. |
| 10,677,866 | B1 | 6/2020 | Rinott et al. |
| 2005/0085720 | A1 | 4/2005 | Jascob et al. |
| 2005/0283074 | A1 | 12/2005 | Jackson et al. |
| 2009/0148014 | A1 | 6/2009 | Kanda |
| 2010/0312095 | A1 | 12/2010 | Jenkins et al. |
| 2012/0049846 | A1 | 3/2012 | Gross et al. |
| 2012/0148153 | A1 | 6/2012 | Kitamura et al. |
| 2013/0051680 | A1 | 2/2013 | Kono et al. |
| 2015/0005756 | A1 | 1/2015 | Tillander et al. |
| 2015/0339510 | A1 | 11/2015 | Bolea et al. |
| 2018/0092518 | A1 | 4/2018 | Yaguchi |
| 2020/0268434 | A1 | 8/2020 | Drown et al. |
| 2020/0273171 | A1 | 8/2020 | Drown et al. |
| 2020/0273175 | A1 | 8/2020 | Drown et al. |
| 2021/0004961 | A1 | 1/2021 | Takahashi et al. |

FOREIGN PATENT DOCUMENTS

| | | |
|---|---|---|
| EP | 2312303 A1 | 4/2011 |
| EP | 2463822 A1 | 6/2012 |
| KR | 20180032156 A | 3/2018 |
| WO | 9609793 A1 | 4/1996 |
| WO | 2008008936 A2 | 1/2008 |
| WO | 2011125991 A1 | 10/2011 |
| WO | 2017189874 A1 | 11/2017 |

OTHER PUBLICATIONS

U.S. Appl. No. 16/282,213, 2020-0268434, filed Feb. 21, 2019, Christine R. Drown et al.

U.S. Appl. No. 16/282,219, 2020-0273171, filed Feb. 21, 2019, Christine R. Drown et al.

Schenck; The role of magnetic susceptibility in magnetic resonance imaging: MRI magnetic compatibility of the first and second kinds; © 1996 American Association of Physicists in Medicine; 36 pages.

Hall; Quantitation of Bubbles using Magnetic Resonance Imaging. University of Cambridge Experimental and Theoretical Physics Tripos—Part III Project. May 2000. 30 pages.

Liu, et al. A novel background field removal method for MRI using projection onto dipole fields. Wiley Online Library. DOI:10.1002/nbm.1670. Published online Mar. 8, 2011. 8 pages.

Grissom. Visualase Bubble Detection. Published Jun. 8, 2018. 13 pages.

Rieke, et al. MR Thermometry. J Magn Reson Imaging. Feb. 2008; 27(2): 376-390. doi: 10.1002/jmri21265. 30 pages.

Poorman, et al. MR imaging simulator and optimized multi-echo z-shimmed sequence for temperature mapping near metallic ablation probes. Proc. Intl. Soc. Mag. Reson. Med. 26 (2018) 1483. 4 pages.

International Search Report and Written Opinion dated May 19, 2020 in corresponding/related International Application No. PCT/US2020/019084.

Siepmann et al: "Phase shift variance imaging—a new technique for destructive microbubble imaging", IEEE Transactions on Ultrasonics, Ferroelectrics and Frequency Control, IEEE, US, vol. 60, No. 5, May 1, 2013, pp. 909-923, XP011507604, ISSN: 0885-3010, DOI: 10.1109/TUFFC.2013.2648 abstract.

Khokhlova et al: "Magnetic resonance imaging of boiling induced by high intensity focused ultrasound", The Journal of the Acoustical Society of America, American Institute of Physics for the Acoustical Society of America, New York, NY, US, vol. 125, No. 4, Apr. 1, 2009, pp. 2420-2431, XP012123209, ISSN: 0001-4966, DOI: 10.1121/1.3081393 p. 2420, col. 1, section 1; p. 2421, col. 1, last paragraph-p. 2421, col. 1, paragraph 1; p. 2425, col. 1, paragraph 3, figure 9.

International Search Report and Written Opinion dated Jun. 12, 2020 in corresponding/related International Application No. PCT/US2020/019080.

Viallon et al: "Observation and correction of transient cavitation-induced PRFS thermometry artifacts during radiofrequency ablation, using simultaneous Ultrasound/MR imaging", Medical Physics, AIP, Melville, NY, US, vol. 37, No. 4, Mar. 11, 2010, pp. 1491-1506, XP012135677, ISSN: 0094-2406, DOI: 10.1118/1.3309439.

International Search Report and Written Opinion dated Jun. 5, 2020 in corresponding/related International Application No. PCT/US2020/019060.

International Preliminary Report on Patentability and Written Opinion regarding Application No. PCT/US2020/019060, dated Sep. 2, 2021.

International Preliminary Report on Patentability and Written Opinion regarding Application No. PCT/US2020/019080, dated Sep. 2, 2021.

International Preliminary Report on Patentability and Written Opinion regarding Application No. PCT/US2020/019084, dated Sep. 2, 2021.

Examination Report corresponding to European Application No. 20712757.2, dated Sep. 13, 2023 (4 pp).

* cited by examiner

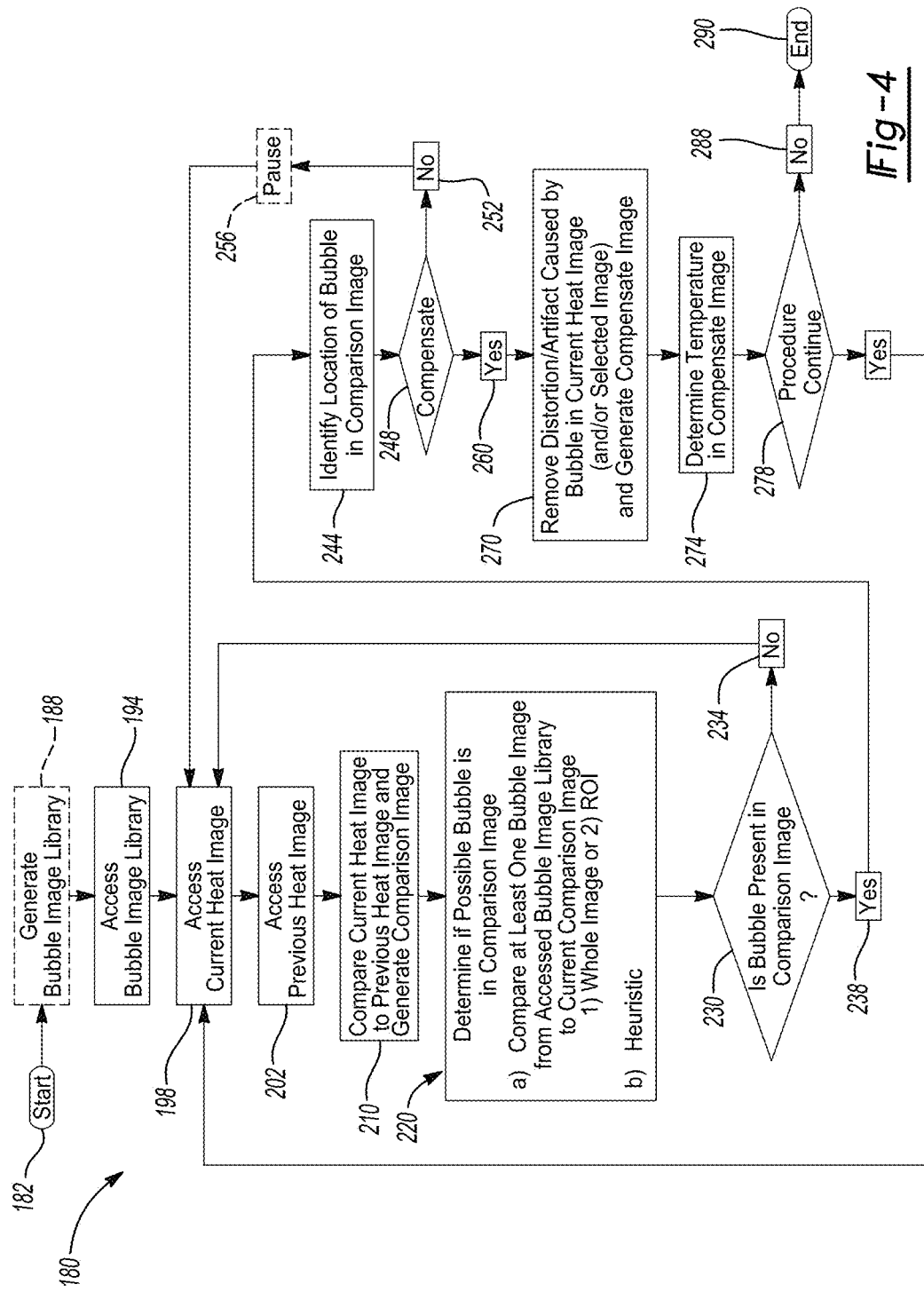

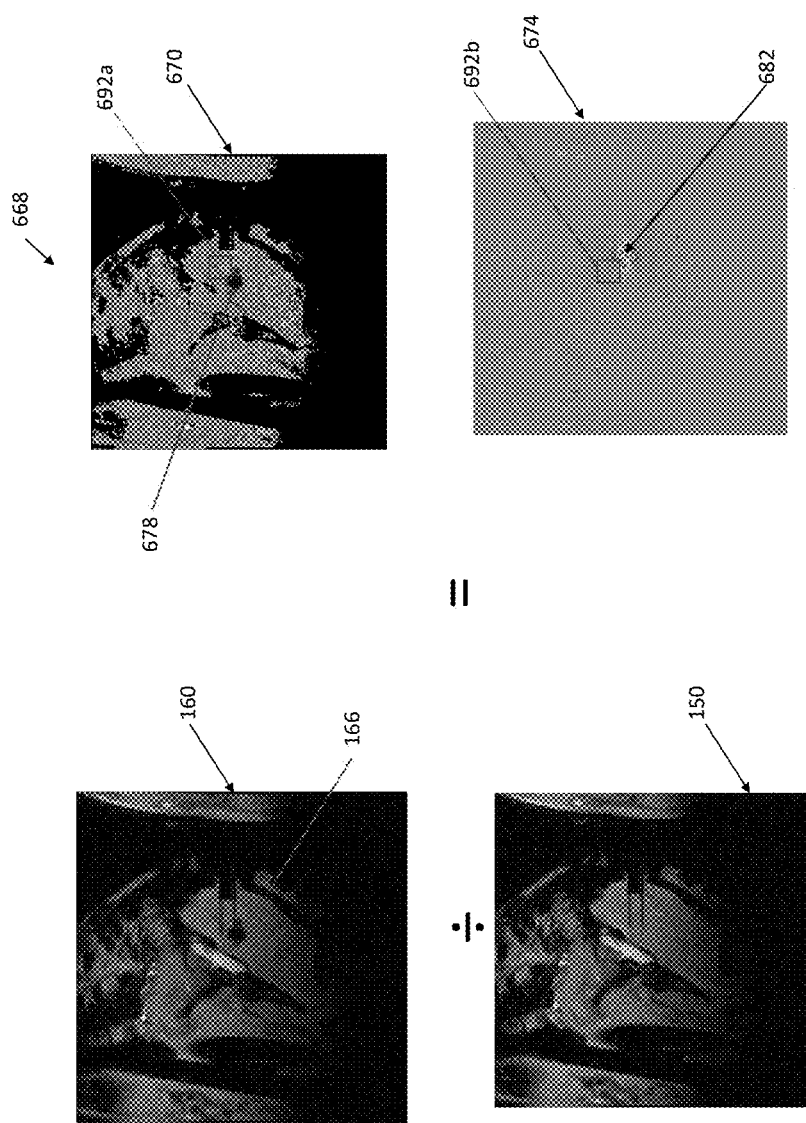

METHOD AND APPARATUS FOR MAGNETIC RESONANCE IMAGING THERMOMETRY

CROSS-REFERENCE TO RELATED APPLICATIONS

This application is a continuation of U.S. patent application Ser. No. 16/282,213, filed Feb. 21, 2019 and includes subject matter similar to that disclosed in concurrently filed U.S. patent application Ser. No. 16/282,193, now Issued U.S. Pat. No. 11,276,174, Issued Mar. 15, 2022 and U.S. patent application Ser. No. 16/282,219. The entire disclosure of the above applications are incorporated herein by reference.

FIELD

The present teachings relate generally to an imaging analysis method and system, and particularly to a method and system for bubble determination.

BACKGROUND

The statements in this section merely provide background information related to the present disclosure and may not constitute prior art.

Imaging techniques have been used to image various portions of the human anatomy. Imaging techniques include ionizing radiation, producing fields relative to a human anatomy, etc. Various types of imaging include imaging by producing fields relative to an anatomy, such as a magnetic field (e.g. magnetic resonance imager (MRI)), and sensing a change in atomic particles of the anatomy induced by the fields. Determining a temperature within an image is performed with various techniques, such as those used in the Visualase® laser ablation system including an MRI-guided, minimally invasive laser ablation system sold by Medtronic, Inc. having a place of business in Minnesota, USA.

SUMMARY

During various procedures, a therapy may be applied to a subject. The subject may include a non-living structure or system, such as an air frame or other construct. Additionally, or alternatively, the subject may include living subjects, such as human subjects. Regardless, in various embodiments, an instrument may be used to apply a therapy to the subject. The therapy may include an application of a heat source or creating heat at a selected location within the subject.

During application of heat, a selected treatment may be carried out, such as an ablation. Ablation may occur within a subject, such as to destroy or remove selected tissue, such as a tumor. In various embodiments, an ablation instrument may be positioned within a brain of a subject to destroy a tumor therein.

A heat application catheter may be positioned within a subject. For example, a cold laser fiber (CLF) system may be used to deliver thermal energy to a tissue. Such CLF systems include those disclosed in U.S. Pat. No. 7,270,656, incorporated herein by reference. The CLF may be used to deliver thermal energy to a selected portion of a subject to ablate tissue within the subject. During ablation, it is selected to determine a temperature near the ablation instrument at a selected sight within the subject. In various embodiments, an image may be acquired of the subject including a region within or near the ablation instrument to calculate or to determine the temperature within the subject.

When acquiring an image of the subject, various items within the image may cause variations within the determined temperature. For example, a bubble may form in a subject during an ablation procedure. During the ablation procedure, the formation of a bubble may allow or require a determination of a temperature in an area of the bubble and/or adjacent to the bubble. The bubble, and a phase shift in selected image modalities (e.g. magnetic resonance imaging), may create a distortion or artifacts that may be accounted for to determine a selected temperature. Accordingly, a system and method is disclosed to detect and/or correct for phase distortion caused by a bubble to determine a temperature within an image at a selected location. The selected location may include the position of the ablation instrument.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4 is a flowchart of a method to determine a bubble and/or compensate therefor;

FIG. 12 is an exemplary application of the method illustrated in the flowchart of FIG. 11.

DETAILED DESCRIPTION

The following description is merely exemplary in nature and is not intended to limit the present disclosure, application, or uses.

Figure 1:
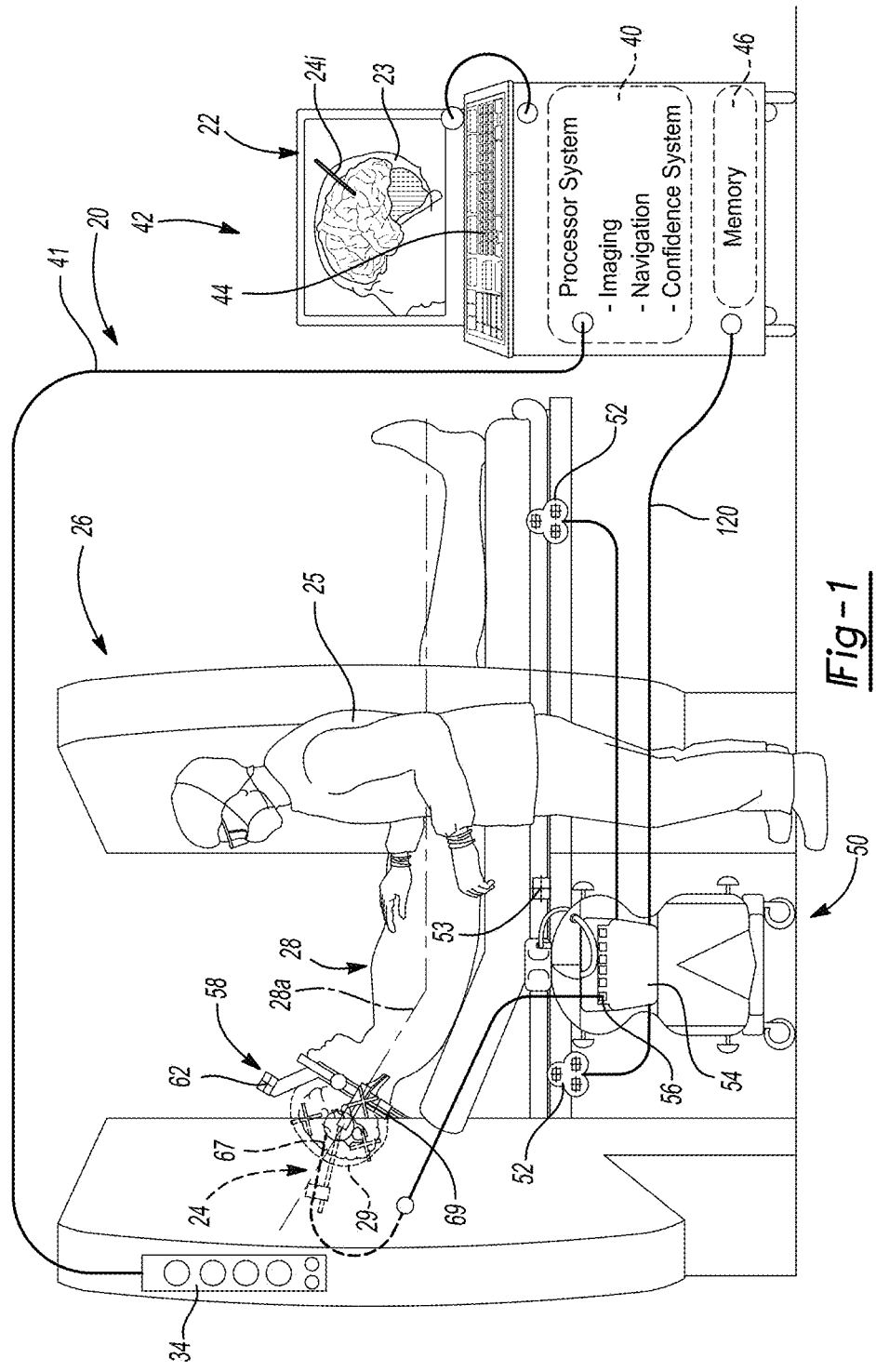
FIG. 1 is an environmental view of a suite, in various embodiments comprising a surgical navigation system and/or imaging system and/or ablation system, according to various embodiments.

With reference to FIG. 1, a procedure may be performed, in various embodiments, with a navigation system 20. The procedure can be any appropriate procedure, such as an ablation procedure, a neural procedure, spinal procedure, and orthopedic procedure. The navigation system 20 can include various components, as will be discussed further herein. The navigation system 20 can allow a user 25, such as a surgeon to view on a display 22 a relative position of an instrument 24 to a coordinate system. The coordinate system can be made relative to an image, such as in an image guided procedure, or can be registered to a patient only, such as in an imageless procedure.

A procedure, as discussed further herein, can be performed using or being assisted with image data. The image data can be image data acquired of a patient 28 using any appropriate imaging system, such as a magnetic resonance imaging (MRI) system 26. The MRI imaging system 26 can be used to acquire selected image data, and/or other types of data such as diffusion data relating to the patient 28. The image data of the subject 28 may include selected types of data, including magnitude and phase data. The various types of data can be used to create images for viewing on the display 22. The image data can be used by the user or surgeon 25, such as during a selected procedure whether or not a navigated procedure. Navigation and imaging systems may include those as disclosed in U.S. Pat. No. 8,340,376, issued Dec. 25, 2012, incorporated herein by reference in its entirety.

The subject 28 may be a human patient, in various embodiments. It is understood, however that the subject 28 need not be a human. Further, the subject need not be a living subject. It is understood, that various systems of constructs (e.g. air frames, test systems, mainframes, etc.). Accordingly, it is understood by one skilled in the art that the subject disclosure is not limited to only a human subject.

The navigation system 20 can be used to navigate or track instruments including: catheters (e.g. ablation and/or delivery), probes, needles, guidewires, instruments, implants, deep brain stimulators, electrical leads, etc. The instrument 24 can be used in any region of the body. Also, any appropriate information about the instrument 24 can be displayed on the display 22 for viewing by the surgeon 25.

Although the navigation system 20 can include an exemplary imaging device 26, one skilled in the art will understand that the discussion of the imaging device 26 is merely for clarity of the present discussion and any appropriate imaging system, navigation system, patient specific data, and non-patient specific data can be used. Image data can be captured or obtained at any appropriate time with any appropriate device.

The navigation system 20 can include the optional imaging device 26 that is used to acquire pre-, intra-, or post-operative or real-time image data of the patient 28. The illustrated imaging device 26 can be, for example, a magnetic resonance imaging device (MRI). Other imaging devices can include an x-ray C-arm having an x-ray source and an x-ray receiving section, computed tomography systems, O-arm® imaging system, etc. The imaging device 26 can be provided to acquire image data of the patient 28 prior to or during a procedure for diagnosis of the patient 28.

Although FIG. 1 illustrates an environmental view showing both the patient, surgeon, navigation system, and other elements, it will be understood that this is merely exemplary of all the portions that can be provided together. For example, an electromagnetic navigation or tracking system may not be provided in a room with the imaging MRI system 26, but is shown in FIG. 1 for illustration and can be separated for use in an actual procedure.

An imaging device controller 34 can control the imaging device 26 to capture and store the image data for use, such as in real time or for later use. The controller 34 may also be separate from the imaging device 26. Also, the controller 34 can be used intra- or pre-operatively to control and obtain image data of the patient 28.

The image data can then be forwarded from the controller 34 to a processor system 40 via a communication system 41. The communication system 41 can be wireless, wired, a data transfer device (e.g. a CD-Rom or DVD-Rom), or any appropriate system. A station 42 may be a work station and may include the processor system 40, the display 22, a user interface 44, and a memory 46. It will also be understood that the image data is not necessarily first retained in the controller 34, but may be directly transmitted to the workstation 42 or to a tracking system 50, as discussed herein.

The work station 42 provides facilities for displaying the image data as an image on the display 22, saving, digitally manipulating, or printing a hard copy image of the received image data. The user interface 44, which may be a keyboard, mouse, touch pen, touch screen or other suitable device, allows a physician or user to provide inputs to control the imaging device 26, via the controller 34, or adjust the display settings of the display 22.

The processor system 40 can process various types of data, such as image data, provided in the memory 46 or from the imaging system 26. The processor system 40 can also process navigation information, such as information provided from the tracking system 50. In addition, navigation processing can include determining a position (e.g. three degree of freedom rotation and three degree of freedom spatial position) of the tracked instruments relative to the patient 28 for display relative to the image data 23 on the display 22. The processor system 40, as discussed herein, may perform or execute instructions to perform various types of analysis such as temperature determination, position determination, etc. It will be understood, each of the processing portions can be processed by separate or individual processors or can be processed substantially sequentially with an appropriate processor.

The optional imaging device 26 can be any appropriate 2D, 3D or time changing imaging modality. For example, an isocentric fluoroscopy, bi-plane fluoroscopy, O-arm® imaging devices (i.e. devices sold by Medtronic, Inc. having a place of business in Minnesota, USA), ultrasound, computed tomography (CT), T1 weighted magnetic resonance imaging (MRI), T2 weighted MRI, positron emission tomography (PET), optical coherence tomography (OCT), single photo emission computed tomography (SPECT), or planar gamma scintigraphy (PGS) may also be used.

The image data obtained of the patient 28 can be used for various purposes. As discussed herein, image data can be obtained for performing a navigated procedure on an anatomy, planning an operation or procedure on an anatomy, and other appropriate reasons. For example, during a neurological procedure, it can be selected to obtain image data of a brain of the patient 28 for viewing during the procedure and, in various embodiments, determining a temperature near a selected portion of the instrument and/or navigating the instrument 24 relative to the image data 23. Further, the acquired image data can be used to plan the movement of the instrument 24 or for positioning of an implant during an operative procedure.

The imaging device 26 can also be used to obtain various types of data other than only image data. The various types of data can be used and overlaid one on another to obtain an appropriate image of the anatomy. For example, a magnetic resonance image can be obtained of a portion of the patient 28, such as a brain 29, for viewing in a selected manner. For example, a 3-D model can be formed of the brain based upon multiple slices of MRI data for displaying on the display 22 during a tracking of a navigated procedure.

Briefly, the navigation system 20 operates to determine the position of the instrument 24 relative to the subject 28 and for viewing relative to the image 23 of the subject 28, as discussed herein. The navigation system 20 creates a translation map between all points in the image data or image space and the corresponding points in the patient's anatomy in patient space (either manually or automatically), an exemplary 2D to 3D registration procedure is set forth in U.S. Pat. No. 7,570,791, entitled "Method and Apparatus for Performing 2D to 3D Registration", issued Aug. 4, 2009, hereby incorporated by reference in its entirety. The points selected can be fiducial marks 69 that include anatomical landmarks or artificial landmarks, such as those disclosed in U.S. Pat. No. 6,381,485, entitled "Registration of Human Anatomy Integrated for Electromagnetic Localization," issued Apr. 30, 2002, hereby incorporated by reference in its entirety. After this map is established, the image space and patient space are registered, that may appear and be determined or selected in both the image space and the subject space. In other words, registration is the process of determining how to correlate a position in image space with a corresponding point in real or patient space. This can also be used to illustrate a position of the instrument 24 relative to the proposed trajectory and/or the determined anatomical target. Registration may occur by the processes and/or system as disclosed in U.S. Pat. No. RE42,226, issued on Mar. 15, 2011, entitled PERCUTANEOUS REGISTRATION APPARATUS AND METHOD FOR USE IN COMPUTER-ASSISTED SURGICAL NAVIGATION, incorporated in its entirety herein by reference. In various embodiments, registration may include a 2D to 3D registration such as an exemplary 2D to 3D registration procedure is set forth in U.S. Ser. No. 10/644,680, filed on Aug. 20, 2003, now U.S. Pat. No. 7,570,791, issued Aug. 4, 2009, entitled "Method and Apparatus for Performing 2D to 3D Registration", hereby incorporated by reference in its entirety.

With continuing reference to FIG. 1, the navigation system 20 can further include the tracking system 50 that includes one or more localizers, such as an electromagnetic (EM) localizer 52, (e.g. which can also be referred to as a transmitter array, a tracking array, tracking coils, or coil array and can include a transmitter and/or receiver coil array). It is understood that other appropriate localizers may also be provide or used, such as an optical localizer. Different localizers may operate in different modalities, such as optical or magnetic field, radar, etc. The tracking system 50 is understood to not be limited to any specific tracking system modality, e.g. EM, optical, acoustic, etc. Any appropriate tracking system modality can be used according to the present disclosure. Moreover, any tracked instrument, such as the instrument 24 and/or a dynamic reference frame (DRF) 58 can include one or more tracking devices that operate with one or more tracking modalities. Thus, the tracking system 50 can be selected to be any appropriate tracking system, including the StealthStation® S7® surgical navigation system that offers both optical and AxiEM™ electromagnetic tracking options.

One skilled in the art will understand that the coil array 52 can transmit or receive, thus reference to the coil array 52 as a transmitter or a transmit coil array is merely exemplary and not limiting herein. The tracking system 50 can further include a coil array controller (CAC) 54 that can have at least one navigation interface or navigation device interface (NDI) 56 for connection of the localizer 52, an instrument tracking device 67 on or associated with the instrument 24, and a dynamic reference frame 58. The coil array controller 54 and the at least one navigation interface 56 can be provided in a single substantially small CAC/NDI container, if selected. The instrument tracking device 67 may be placed or associated with the instrument 24 in any appropriate manner or position to allow for determination of a selected portion (e.g. terminal end) of the instrument 24. In various embodiments, the tracking device 67 may include a coil positioned at or near a terminal end of the instrument 24.

In an optional optical system, generally an optical localizer includes one or more cameras that "view" the subject space. The cameras may be used to determine position of the tracking element relative to the cameras. Tracking devices include members that are viewable by the cameras. The optical tracking devices may include one or more passive or active portions. An active tracking device can emit a viewable wavelength, including infrared wavelengths. Passive tracking devices can reflect selected wavelengths, including infrared wavelengths.

The tracking system can be included in the navigation system 20 and may include, in various embodiments, an EM localizer, which may be the coil array 52. The EM localizer 52 can include that described in U.S. Pat. No. 7,751,865, issued Jul. 6, 2010, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997, each of which are hereby incorporated in their entirety by reference. The localizer may also be supplemented and/or replaced with an additional or alterative localizer. As is understood the localizer 52, according to any of the various embodiments, can transmit signals that are received by the dynamic reference frame 58, and a tracking device that is associated with (e.g. connected to) the instrument 24. The dynamic reference frame 58 and the tracking device can then transmit signals based upon the received/sensed signals of the generated fields from one or more of the localizers 52. Tracking systems, including the optical tracking system, can include the StealthStation® S7® Surgical Navigation System, sold by Medtronic Navigation, Inc. The optical localizer can view the subject space and the tracking devices associated with the DRF 58 and/or the instrument 24.

The work station 42, either alone or in combination with other appropriate processor systems, including the coil array controller 54 and the controller 34, may identify the corresponding point on the pre-acquired image or atlas model relative to the tracked instrument 24 and display the position on display 22 and relative to the image data 23. This identification is known as navigation or localization. An icon representing the localized point or instruments is shown on the display 22 within several two-dimensional image planes, as well as on three dimensional (3D) images and models. In order to maintain registration accuracy, the navigation system 20 can continuously track the position of the patient 28 with the dynamic reference frame 58. The position of the instrument 24 may be transmitted from the instrument tracking device 67 through a communication system, such as a wired or wireless communication. The tracking devices, or any other appropriate portion, may employ a wireless communications channel, such as that disclosed in U.S. Pat. No.

6,474,341, entitled "Surgical Communication Power System," issued Nov. 5, 2002, hereby incorporated by reference in its entirety, as opposed to being coupled with a physical transmission line.

The instrument 24 used in a procedure can be any appropriate instrument (e.g., a catheter, a probe, a guide, etc.) and can be used for various procedures and methods, such as delivering a material, ablation energy (e.g. heat), or providing electrical stimulation to a selected portion of the patient 28, such as within the brain 29. The material can be any appropriate material such as a bioactive material, a pharmacological material, a contrast agent, or any appropriate material. As discussed further herein, the instrument 24 can be precisely positioned via the navigation system 20 and otherwise used to achieve a protocol for positioning and/or applying a treatment relative to the patient 28 in any appropriate manner, such as within the brain 29. The instrument 24 may also include a brain probe to perform deep brain stimulation and/or ablation.

Figure 2:
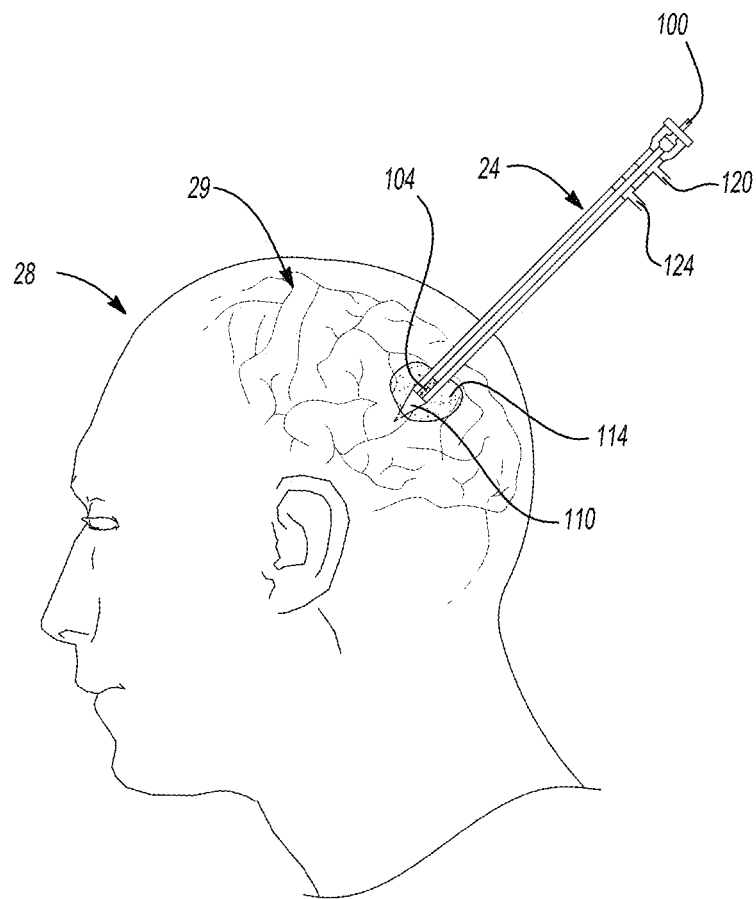
FIG. 2 is a schematic illustration of a subject and an instrument positioned relative thereto, according to various embodiments.

With reference to FIG. 2, the instrument 24 may be positioned within the brain 29 of the subject 28 such as according to various techniques, such as those disclosed in U.S. Pat. No. 7,270,656, incorporated herein by reference. Further, the instrument 24 may include various features such as an energy delivery or transfer system or mechanism 100 which may include a fiber optic cable to transmit laser energy to a distal end 104 of the instrument. The distal end 104 of the fiber optic member 100 may be near a terminal end 110 of the instrument 24. The instrument 24, therefore, may generate heat or thermal energy near a tumor 114 within the subject 28, such as within a brain 29. Temperature near the terminal end 110, such as within the tumor 114, may be modulated by providing or varying the amount of energy through the energy transfer system 100 and/or transferring or passing a cooling medium through the instrument 24. Passing a cooling medium may include providing a cooling medium to a cooling medium inlet 120 that may pass through a cooling medium return 124. The cooling medium can be any appropriate material, such as water, saline, or the like. Nevertheless, thermal energy may be delivered to the subject 28 to perform a therapy on the tumor 114 within the subject 28. During therapy to the subject 28, the imaging system 26 may be used to image the subject 28 to determine a temperature at or near the end 104 and/or the terminal end 110.

As discussed above, the instrument 24 may be tracked relative to the subject 28, such that the position of the distal end 110 and/or the end of the energy delivery system 100, may be determined. Accordingly, images acquired with the imaging system 26 may be registered to the subject 28 and/or to the instrument 24. This allows the navigated position of the instrument 24 to be determined relative to the images acquired of the subject 28. The position of the instrument 24 may be displayed on the display device 22, such as with a graphical representation 24i' displayed on the display system 22, such as superimposed on the image 23.

During an ablation procedure, as illustrated in FIG. 1, the user 25 may apply energy to the subject 28 with the instrument 24 at a selected rate or time to heat a portion of the subject. During the heating, a heating image is acquired at a selected rate. For example, heating images may be acquired at a rate of about every five seconds, every ten seconds, or any selected period of time. Accordingly, during the application of thermal energy to the subject 28, heat images are acquired to determine the temperature at the location of the instrument within the subject 28.

A heat image may be an image acquired with the imaging system 26 for determining a temperature within the subject 28. The heat image may include various information, such as diffusion information or relaxation times, or phase changes that may be analyzed to determine a temperature and/or a temperature change from a prior heat image. Thus, the heat image may be used to determine a temperature or temperature change on a pixel or voxel basis relative to a prior image or alone. Thus, a heat image may include an image acquired of the subject 28 for determining a temperature therein.

A heat image may be displayed on the display 22, or any other appropriate display. For example, a heat image may be displayed on the display device 22, as illustrated in FIG. 3. The heat image may include a first heat image 150. The first heat image may include an image of the brain 29 as the image 23. The heat image 150 may also include image data or an image of the instrument 24 as the instrument 24a. It is understood that the instrument 24 may appear according to different shapes or geometries based upon the particulars of the instrument 24, and the illustration as one or a plurality of legs in FIG. 3A is merely exemplary. However, the heat image 150 may be displayed for viewing by the user 25 to illustrate substantially the magnitude in the image. The heat image 150 may be slice, such as an MRI image slice, where each voxel or pixel includes an intensity, where a higher intensity is a lighter color and a lower intensity is a darker color. The first heat image 150 may be a baseline or first heating image. In various embodiments, therefore, a second heating image may be acquired.

Figure 3B:
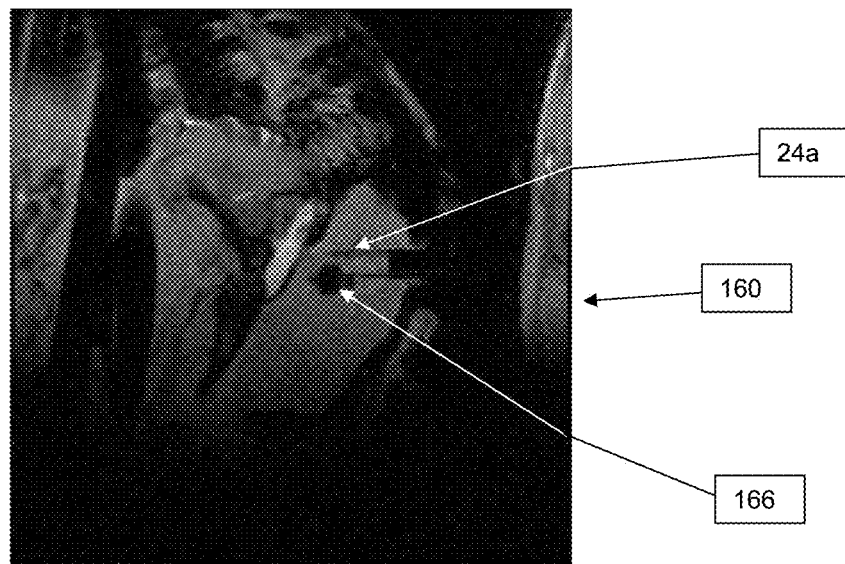
FIG. 3B is an image of a subject with an instrument therein having a low intensity region near the instrument.
Figure 3A:
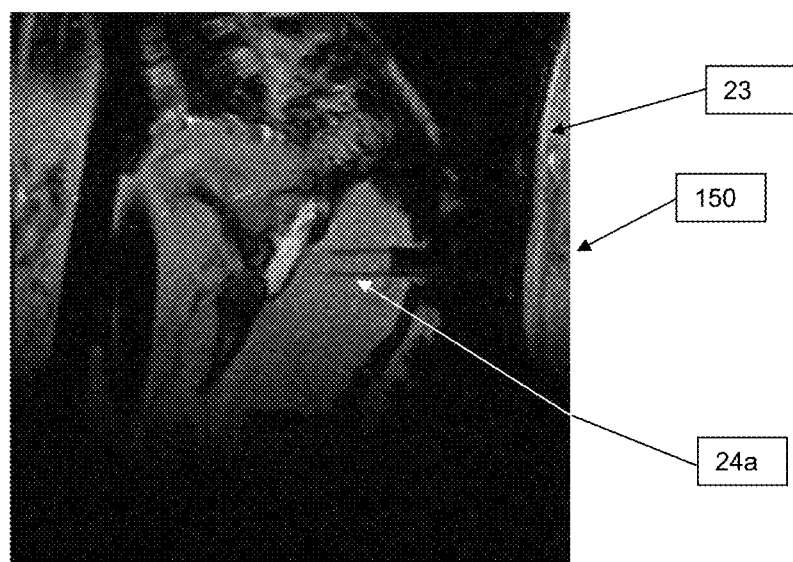
FIG. 3A is an exemplary image of a subject with an instrument positioned within tissue thereof, according to various embodiments.

With reference to FIG. 3B, a second heat image 160 is illustrated. The heat image 160 may also illustrate the instrument 24a. Near or adjacent to the instrument 24a is a dark region or low intensity region 166. The low intensity region 166 may be a bubble that is formed near or adjacent to the instrument 24 within the subject 28. The low intensity region 166 may appear in the heat image 160 as a dark or low intensity portion near the instrument 24a. The identification of the low intensity region 166 as a bubble, however, may be difficult with only viewing the display device 22. Moreover, a temperature at the portion including the bubble or low intensity region 166 may be calculated even with the presence of the low intensity region 166, as discussed further herein.

The bubble, without being limited by the theory, may be caused by heat caused in various tissues or materials. The materials may cause gas to form within a volume. The volume may be bounded by the material in which the instrument 24 is placed. The bubble, therefore, in the anatomy may be caused by various local conditions therein. In an image, such as a MRI image, as discussed herein, the bubble may be a region devoid of significant signal due to low proton density and/or rapid motion, surrounded by an image phase/frequency disturbance due to the difference in magnetic susceptibility between adjacent tissue and the bubble volume. The bubble in this context may appear due to the conditions associated with a selected therapy to the subject, such as heat. A specific size and constitution of a given bubble depends on a local environment (e.g. tissue) as well as the therapy (e.g. heating) conditions.

As discussed further herein, the first heat image 150 may be acquired at any time during the application of the thermal energy to the subject 28. Further, the second heat image 160 may be any subsequent, such as an immediately subsequent image, and may also be referred to as a current heat image. Accordingly, during the application of the thermal energy to the subject, heat images may be acquired in sequence. Each heat image that is acquired that does not include a bubble may be a first or baseline image and the subsequent image, such as an immediately subsequent image, that includes a bubble may be the second heat image 160. It is understood, however, that the baseline or first heat image 150 may also be an initial image acquired of the subject 28. In various embodiments, the first heat image 150 may always be the first or baseline image and every subsequent image is compared thereto for determination and/or to assist in determination of a bubble present with the image.

As discussed above, with reference to FIG. 3A and FIG. 3B, a dark region or artifact 166 may appear in the heat image 160. The region spot 166 may be a bubble or other artifact feature that may reduce a confidence in a temperature determined using the heat image 160. Accordingly, with reference to FIG. 4, a bubble determination and/or compensation method 180 is illustrated. The bubble detection and/or compensation method 180 may include a plurality of steps or procedures, as discussed herein, that may be included in various sub steps or procedures, as discussed further herein, but starts in start block 182. Accordingly, the method 180 may be understood to be an overall or inclusive method or algorithm for detecting and/or compensating for a bubble in a heat image that may include various subroutines or elements that includes more than one step, as discussed herein. Further, it is understood that the method 180 may be implanted as instructions that are executed by a selected processor system, such as the processor system 40. The method 180 may be substantially automatically executed when a selected heat image or comparison image is accessed or acquired.

Initially, a bubble image library may be generated in block 188. Generation of the bubble image library may not be required for the detection and compensation method 180, but may be included for clarity and completeness for the current discussion. Thus, a library may be generated such as in real time and/or prior to performing of a selected procedure, such as an ablation procedure, as discussed above.

Regardless of whether the bubble library is generated immediately before or at a prior time, the bubble image library may be accessed in block 194. The bubble image library 188, therefore, may be stored on a selected or in a selected memory system to be accessed by a processor, such as the processor system 40 discussed above. It is understood that the processor system 40 may include a plurality of processors, and the detection and compensation method 180 may be executed by a processor that is included with, separate from, and/or in communication with the processor system 40. Regardless, an appropriate processor may execute instructions to access the bubble image library in block 194. The bubble image library accessed in block 194 may include appropriate bubble images that may be based upon selected models that are used to generate the bubble library in block 188. The bubble image library accessed in block 194 may include more than one type of image, such as magnitude and/or phase data. The bubble image library access in block 194 may include or be generated based upon magnetic resonance imaging systems.

The bubble image library may be accessed in block 194 at any appropriate time. It is illustrated in the method 180 as being initially accessed, however, it need not be accessed until compared to a selected image, such as during a comparison or prior to a comparison of a bubble image from the bubble image library to a selected image, as discussed further herein.

Regardless of the timing of accessing the bubble library in block 194, accessing a current heat image in block 198 may occur. The current heat image accessed in block 198 may be a heat image that is acquired by or at the direction of the user 25 during a selected procedure. The current heat image is acquired to attempt to determine a temperature within the subject 28 at or near an ablation region of the subject relative to the instrument 24. As discussed above, the current heat image may be used to determine a current temperature or a temperature at the time of acquiring the heat image. Generally, the current heat image may be acquired at a selected rate, such as five seconds after an immediately previous heat image. It is understood, however, that the current heat image may be acquired at any appropriate time relative to a previous heat image, as may be selected by the user 25.

Accessing a previous heat image in block 202 may also occur. The previous heat image may be any appropriate previous heat image, such as an immediate prior heat image and/or any heat image acquired prior to the current heat image. For example, during various procedures, an initial or prior to ablation heat image may be acquired of the subject 28. The previous heat image may be a heat image acquired at the initial or prior to ablation or therapy. In various embodiments, however, the previous heat image may be a heat image that is acquired immediately prior to the access current heat image in block 198.

Regardless of the timing of the collection of the current heat image and the previous heat image, the two accessed heat images may be compared in block 210. The comparison of the current heat image and the previous heat image in block 210 may be used to generate a comparison image. The comparison image may be generated in any appropriate manner, as discussed further herein. Generation of the comparison image may attempt to determine differences between the current heat image and the previous heat image. The differences may include magnitude and/or phase differences between the current heat image and the previous heat image. The generated comparison image may include these differences for further analysis, as also discussed herein.

The generated comparison image may then be analyzed to determine if a bubble is present or possibly present in the comparison image. In various embodiments, the comparison image may be compared to at least one bubble image accessed from the bubble image library to the generated comparison image in block 220. The comparison of the at least one bubble image to the generated comparison image may be done in any appropriate manner, as also discussed herein. For example, the accessed bubble image library may include bubble images that include magnitude information and/or phase change or drift that may be caused due to the presence of a bubble. In comparing the bubble image from the access bubble image library to the generated comparison image in block 220, a determination of whether a bubble is present in the comparison image may be made in block 230. The determination of whether a bubble is present in the generated comparison image may be based upon the comparison of the bubble image from the bubble image library, as discussed further herein. In various embodiments, the comparison image may also be analyzed or compared in a heuristic manner, such as analysis of the image with a selected system, as discussed herein.

The determination of whether a bubble is present may be made in block 230 based upon the comparison in block 220. If no bubble is present, a NO-path 234 may be followed to access a current heat image in block 198. Again, accessing a current heat image in block 198 may be made at any appropriate time, and may be a current heat image that may be after a heat image that is accessed in a first iteration. Accordingly, it is understood, that the method 180 may be an iterative process that may be performed during a selected procedure, such as during an ablation procedure on the subject 28. The current heat image that is accessed in block 198 may be any appropriate current heat image that may be at a time between the initiation of therapy and the termination of a therapy and any appropriate intermediate point therein.

If a determination is made in block 230 that a bubble is present, a YES-path 238 may be followed. The YES-path 238 may be followed to identify a location of the bubble comparison image in block 244. Identifying a location of the bubble in the comparison image in block 244 may include identifying the bubble in the comparison image for further analysis and determination of the current heat image or the generated comparison image. Identification of the location of the bubble in block 244 may include identifying that a bubble exists and/or the pixels or voxels in the generated comparison image and/or access current heat image that belonged to the bubble and/or are affected by the bubble. Thus, identifying location of the bubble in the comparison image may allow for further compensation of the presence of the bubble in the current heat image, if selected.

Accordingly, after identifying the location of the bubble in block 244, a compensation determination block 248 allows for a determination of whether compensation will occur. The user 25 may select to compensate temperature determination, as discussed herein, for the identified location of the bubble and/or may determine to terminate therapy for a selected period of time to allow the bubble to dissipate.

Accordingly, the compensation determination in block 248 may allow the user to determine to not compensate and follow a NO-path 252 to perform various selected procedures. Additionally, when the NO path 252 is followed the method 180 may iterate, as noted herein. Further, the bubble may only be identified in the image and identified to the user 25. The identity to the user may be displayed with the image 23 and/or separately therefrom. Thus, the method 180 may be to only identify a bubble or possible bubble, in various embodiments.

When the NO path is followed 252, various other procedures or steps may occur. For example, pausing a procedure in optional pause block 256. After pausing the procedure in pause block 256, for a selected period of time (e.g. about one second to about one minute, or any appropriate time), the user 25 and/or the ablation system may again access a current heat image in block 198. Again, the current heat image accessed in block 198 may be acquired after the previous current image in block 198, such as after the pause 256. Again, a determination of whether a bubble is present in one or a current heat image may be made and whether compensation will be made in block 248. Accordingly, if compensation is not made, the identification of the bubble and the current heat image may allow the user 25 to pause or allow for the bubble to dissipate. The system, however, executes the method 180, may be used to automatically identify whether a bubble exists within the current heat image based upon the algorithm method 180.

The compensation determination in block 248 also allows for compensation to occur and thus a YES-path 260 may be followed. If compensation is selected in block 248, the YES-path 260 may be followed to remove distortion/artifact caused by the bubble in the current heat image and/or other selected image, such as the generated compensation image in block 270. Removal of the distortion or artifact caused by the bubble in the current heat image in block 270 may be made according to selected techniques, including those discussed further herein, such as removing the phase distortion and/or magnitude distortion caused by the identified bubble at the identified location. The compensate image may include the distortion or artifact removed that is generated in block 270, such as through subtraction of the identified bubble.

Once the distortion is removed in block 270, a determined temperature in the compensate image may be made in block 274. The determined temperature in block 274 may be used for performing the selected procedure, such as determining a temperature at or near the end of the instrument 24. As discussed above, the ablation procedure may occur or proceed when a selected temperature is achieved or in attempt to achieve a selected temperature. Accordingly, determining a temperature, as discussed herein, in the compensate image in block 274 may be used for performing the procedure, such as an ablation procedure, on the subject 28.

The determined temperature in the compensated image may then determine whether a procedure may continue in block 278, according to selected criteria (e.g. temperature, duration, etc.). Determination of whether the procedure continues in block 278, however, may again be selected based upon the user 25 and/or performing of a selected procedure, including the ablation procedure.

If a determination is that the procedure is to continue, a YES-path 282 may be followed. The YES-path 282 may again follow to accessing a current heat image in block 198. The current heat image may be again acquired at any appropriate time, such as after the identification and/or compensation of a bubble in a previous current heat image. Accordingly, the current heat image accessed in block 198, when following the YES-path 282, may again be understood to create an iterative process of the method 180.

If selected, however, a NO-path 288 may be followed, such as the procedure should terminate. When terminating the procedure, the NO-path 288 may follow to an end block 290. Ending the method 180 may include completing a procedure on the subject 28, such as removing the instrument 24, or other appropriate steps. Further ending the procedure 180 at block 290 may include terminating application of energy for a selected procedure, at a selected time, restarting a procedure, or other appropriate procedure steps.

As noted above, the method 180 may include various sub-steps or sub-routines, steps may be executed by a processor system, including those discussed above and herein. In various embodiments, therefore, the bubble image library may be generated in block 188. With continuing reference to FIG. 4 and additional reference to FIG. 5, the generation of the generated bubble image library 188 is described in greater detail. The generated bubble image library method 188 may be performed automatically with the processor system, such as the processor system 40 and/or with input by the user 25 and/or appropriate user. Generally, the bubble image library is generated based upon forming a plurality of bubble images based upon a model, including altering a model based upon size and/or orientation of the bubble in an image.

The bubble library method may initiate in start block 300. Thereafter, a bubble model may be generated and/or accessed in block 304. The accessed bubble model may be based upon selected information, such as a selected definition of a bubble. In various embodiments a definition of a bubble may include or be defined by Equation 1:

$$\Delta f_{bubble} = -r^3 \frac{\gamma}{2\pi} B_0 d_\chi \frac{2z^2 - x^2 - y^2}{3(x^2 + y^2 + z^2)^{5/2}}$$

Equation 1 may be used to define the frequency shift of a bubble in hertz when the bubble exists in a substantially homogeneous structure, such as the brain 29. Equation 1 assumes or acknowledges that a bubble may be substantially gas or air and that a difference between magnetic susceptibility between air or gas tissue may be about 9 ppm. Accordingly, the magnetic susceptibility of the air in the bubble may be about 9 ppm less than the surrounding tissue, therefore the $d_x = -9$ ppm. In various assumptions a gyromagnetic ratio is $\gamma = 42.58$ megahertz per tesla. $B_0$ is the field strength in tesla of the imaging system 26, such as a MRI scanner. Further, r is the radius of the bubble and x, y and z are in centimeters and indicate a position of the bubble, where z is the $B_0$ direction. Frequency, f, is in hertz. Generally, the bubble is assumed to be substantially spherical therefore in a grid of x, y and z coordinates the values within a bubble are defined or identified as zero and masked out.

Accordingly, Equation 1 may be used to identify or calculate an image model over a three-dimensional grid (x, y, z) locations within a slice. As noted above, an MRI may be used to generate the image data and the MRI image may have a selected slice width. Accordingly, the MRI slice image may have a three-dimensional volume through which Equation 1 may be used to calculate the residence frequency offset $\Delta f$. A total frequency offset at a selected location (x, y, z) during an excitation pulse is given by Equation 2:

$$\Delta f(x, y, z) = \frac{\gamma}{2\pi} G_z Z + \Delta f_{bubble}(x, y, z)$$

In Equation 2 $\gamma$ is the same as noted above, $G_z$ is the frequency shift with a slice gradient amplitude, z is the spatial location of the slice, and $\Delta f_{bubble}$ is from Equation 1. Thus, given this frequency map and a frequency profile of an RF pulse in an MRI, interpolation may be used to calculate a slice profile for each spatial location of the bubble, which may be denoted as (x, y, z). To determine a slice profile near a bubble, various assumptions may be made, such as a three millisecond per time bandwidth product of an RF pulse and a small excitation or flip angle (e.g. about 10 degrees to about 40 degrees, including about 25 degrees) may be assumed along with a three millimeter slice thickness.

Accordingly, a bubble image, which may also be referred to as a slice profile of the bubble, may be illustrated by Equation 3:

$$s_{TE}(x,y,z) = x(x,y,z) e^{i2\pi TE \Delta f(x,y,z)}$$

In Equation 3, the slice profile may be formed or advanced to an echo-time represented by TE, therefore the spatial profile given by Equation 3 may be at the echo-time of the imager. In Equation 3, the term s(x, y, z) is the signal at the end of the excitation pulse and the exponential accounts for time passing to the echo-time. Accordingly, TE is the time past or accounts for the time past to the echo-time of the signal such that the spatial profile is advanced to the echo-time. Then summing across a slice profile is given by $\Delta f(x, y, z)$ and allows for generating the slice profile of the bubble. A convolution to average multiple x and y location or direction spins may be made to account for a signal loss due at each of the x, y locations.

Further, it is understood that the model of the bubble may be based upon accounting for the profile effects within the slice and/or without. Nevertheless, the bubble image may be based upon the accessed model, as discussed above.

The accessed model in block 304, as described above, may then be used to generate a plurality of bubble images in block 310. The plurality of bubble images may be based upon altering various characteristics of the bubble model. For example, a change in radius of the bubble may be used to identify or determine various sizes of the bubbles. For example, the radius may be given in a selected dimension, such as voxels, and may range between about 1 voxel and about 50 voxels, including about 2 voxels and about 12 voxels, and further including a discrete number of voxels between 2 and 12. For example, the bubble library may include 10 bubbles each differing by 1 voxel with the smallest bubble having a radius of 2 voxels and the largest bubble having a radius of 12 voxels. Further, the bubble models may be rotated or angled relative to the axis of the imager, $B_0$ axis. Each of the bubbles of different radius may be rotated a selected angle $\theta$. The amount of rotation may be any appropriate amount. For the bubble library, for example, each bubble may have in plane rotations of about −45 degrees to about +45 degrees in 15 degree steps. The amount of rotation at x and z coordinates may be given by $X_{rot}$ and $Z_{rot}$ in Equation 4 and Equation 5, respectively:

$$X_{rot} = X \cos(\theta) - Z \sin(\theta)$$

$$Z_{rot} = X \sin(\theta) - Z \cos(\theta)$$

Thus, each of the bubble images may include a bubble of a selected radius and/or selected angle rotation relative to the $B_0$ axis. Each of the plurality of bubble images, therefore, may be saved in the bubble image library that may be accessed in block 194, as discussed above. Thus the plurality of images may be saved in the bubble library in block 314 that may be accessed in block 194, as illustrated in FIG. 4.

After saving a plurality of generated bubbles in a library in block 314, a determination of whether more bubbles are selected is made in block 318. If more bubbles are selected, a YES-path 320 may be followed to block 310 to generate a plurality of bubble images, which may be in addition to a previous plurality of bubble images. If a determination in block 318 is that no more bubbles are selected, a NO-path 324 may be followed to end in block 330. The bubble image library may be formed at any appropriate time, such as prior to the beginning of a procedure, during a procedure, or at any selected time. Regardless, the bubble image library may be generated as discussed above and may be used during a temperature sensing process.

Figure 5:
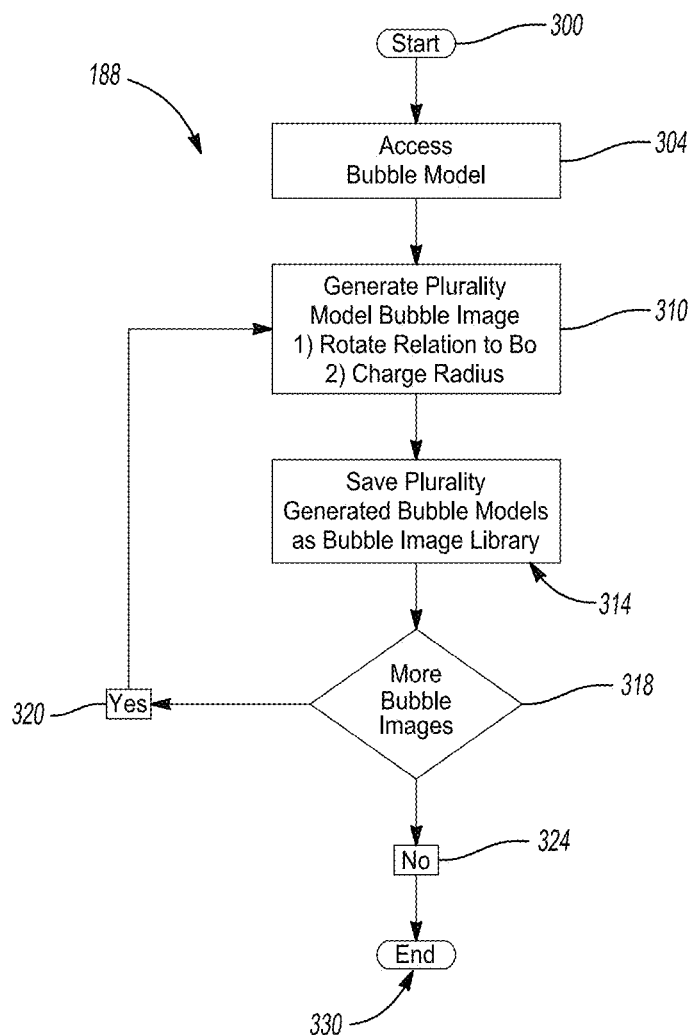
FIG. 5 is a detailed flowchart for a method of generating a bubble image library.
Figure 6:
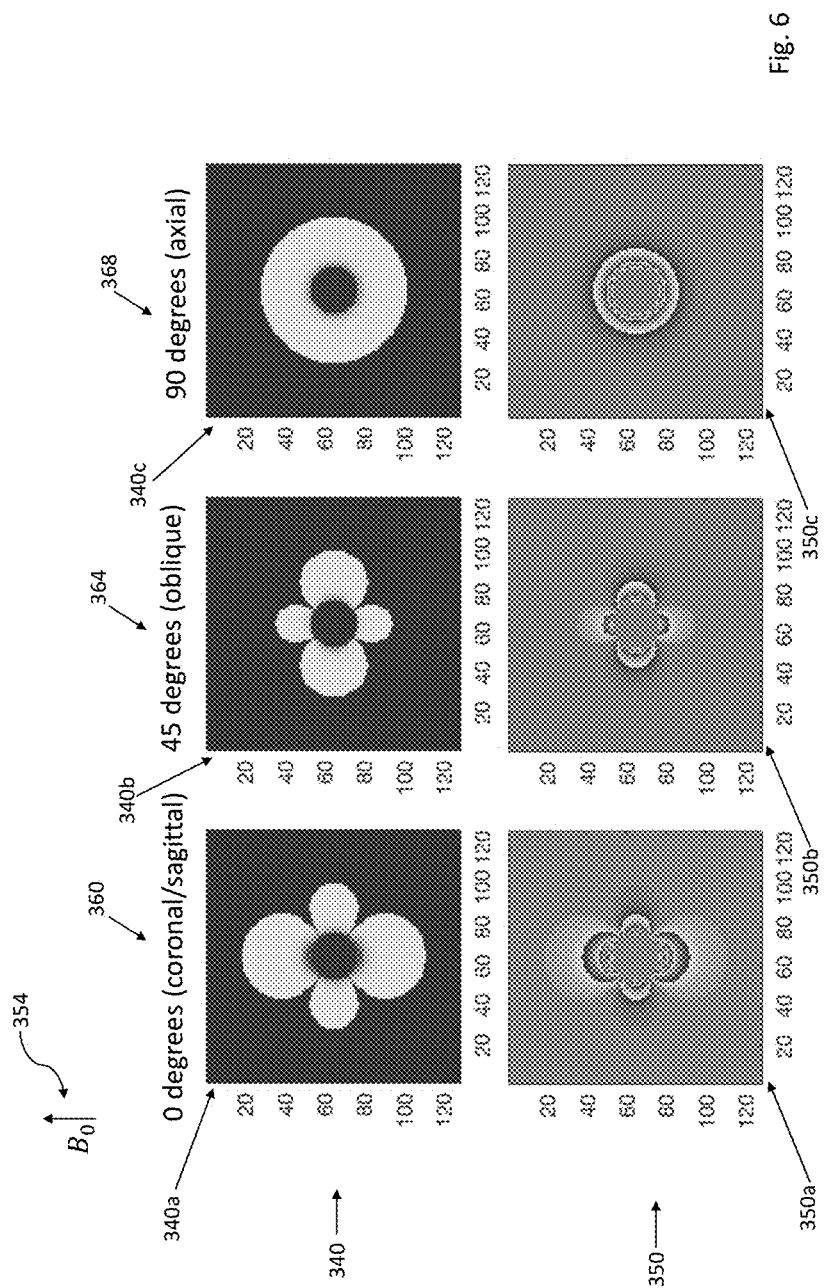
FIG. 6 is an example of bubble images in a bubble image library.

With continuing reference to FIG. 5 and additional reference to FIG. 6, the bubble library may be formed to include bubble images that include both magnitude and phase differentiation. As understood by one skilled in the art, the phase in an MRI may relate to an encoding due to a resonance in light of the MRI imaging process. Generally, MRI imaging may include both a frequency encoding and a phase encoding, to determine information regarding each pixel or voxel in a slice image. Accordingly, phase encoding may be used to assist in determining a temperature at a selected voxel within the image. As illustrated in FIG. 6, the model accessed in block 304, may be used to generate library images. In FIG. 6, library images of a bubble of a selected radius are illustrated as a magnitude image in a first row 340 and a phase in a second row 350. The bubble image in the bubble image library may identify gradations or amounts of change as well. As illustrated in FIG. 6, an amount or variation in the magnitude and phase variance may be included in the bubble image in the bubble image library and for correlation to the comparison image, as discussed herein. The bubble library may further include the bubble model that is rotated relative to the axis $B_0$ 354 of the imaging system. Accordingly, the library images may include a plurality of images that are rotated in both magnitude and phase.

As illustrated in FIG. 6, a first column 360 illustrates a magnitude image 340a and a phase image 350a that are parallel with the axis $B_0$ of the imager. In a second column 364 a magnitude image 340b and a phase image 350b is illustrated for the bubble. Finally, in a third column 368 the bubble is illustrated at substantially 90 degrees or perpendicular to the axis $B_0$ as a magnitude image 340c and a phase image 350c.

The bubble image library may include a plurality of images more than the six illustrated in FIG. 6, as discussed further herein. Regardless, the bubble library may include a plurality of images that allow for identification and analysis of a heat image, as discussed further herein. It is understood that an identification system may further interpolate between different bubble images to assist in identifying a bubble in a current heat image or comparison image.

Figure 7:
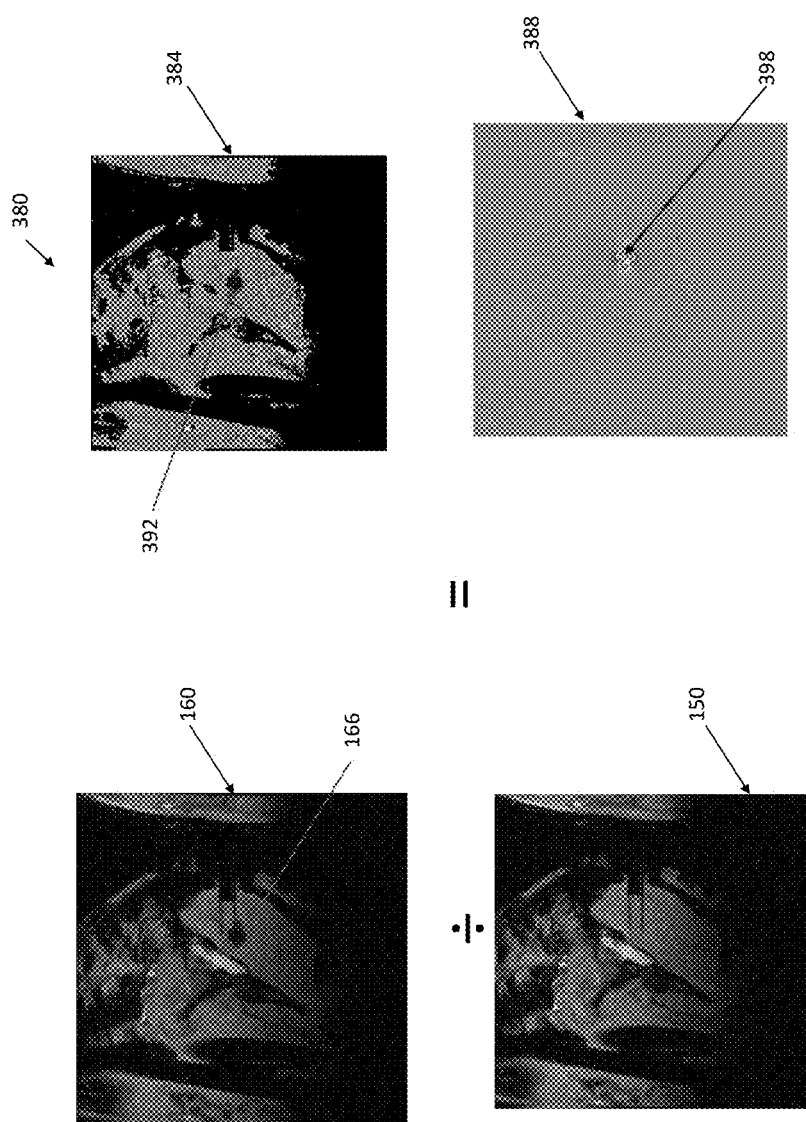
FIG. 7 is a schematic illustration of a comparison and identification, according to various embodiments.

With continuing reference to FIG. 4 and additional reference to FIG. 7, the heat images that may be accessed in blocks 198 and 202, may be similar to the heat images illustrated in FIGS. 3A and 3B. Accordingly, a previous heat image 150 and a current heat image 160 are illustrated. The current heat image 160 may be recalled in block 198 while the previous heat image 150 may be recalled or accessed in block 202, as illustrated in FIG. 4.

The two images may be compared to one another in block 210, as discussed above. To compare the two images to one another a ratio may be made between the current heat image 160 and the previous heat image 150. That is, the current heat image 160 may be divided by the previous heat image 150. In dividing the current heat image 160 from the previous heat image 150, a ratio of each of the voxels or pixels within the current heat image 160 may be determined. During acquisition of image data of the subject 28, the subject 28 may be held substantially fixed relative to the imaging system 26. Accordingly, images may be acquired over time of the subject 28 that may be substantially registered to one another and in series. Accordingly, a pixel or voxel location in the current heat image 160 may be known relative to a pixel or voxel in the prior heat image at the same position. Thus, a ratio between the two may be determined. It is understood that other appropriate differences or comparisons may be made, and a ratio is merely exemplary. Nevertheless, the ratio of the current heat image 160 to the previous heat image 150 may result in resultant images in column 380, illustrated in FIG. 7.

The resultant images or generated comparison images may include a magnitude generated comparison image 384 and a phase comparison image 388. The magnitude comparison image 384 may include a ratio of each voxel density or intensity between the current heat image 160 and the prior heat image 150. The pixel or voxel intensities may be displayed in the magnitude comparison image 384 for viewing by the user 25, such as on the display 22. It is understood, however, that the generated comparison image 380 may simply be used for analysis by the workstation 42 to identify a bubble, if present, and compensate therefore.

The generated comparison images 380 may also include the phase comparison image 388. As discussed above, the image data acquired with the MRI system 26 may acquire different types of data including the magnitude image data, as illustrated in the magnitude comparison image 384 and phase encoded image data as shown in the comparison image 388.

As illustrated in FIG. 7, a hole or dark region 166 is present in the image 160. The resultant comparison images may also include or identify a magnitude ratio where the magnitude comparison image 384 includes a dark or low intensity region 392. The low intensity ratio region 392 illustrates that there is a small ratio between the current heat image 160 and the prior heat image 150. In various embodiments, as discussed further herein, a magnitude threshold may be used to assist in determining whether a data set, such as the comparison data set 380, includes a bubble. A magnitude threshold may be about 0.20 to about 0.90, and further include about 0.50 to about 0.750, and further include about 0.65. In various embodiments, therefore, a decrease in signal of about 32% to about 40%, and further including about 35%, may be used to assist in identifying a relevant comparison data set for including a bubble.

Further, the phase comparison image 388 may also include a region of phase differentiation or comparison 398. The phase comparison region 398 may also illustrate the phase variations between the current heat image 160 and the previous heat image 150. Thus, both a magnitude and a phase difference may occur between the current heat image 160 and the prior heat image 150 when a bubble occurs in the subject 28.

Figure 8:
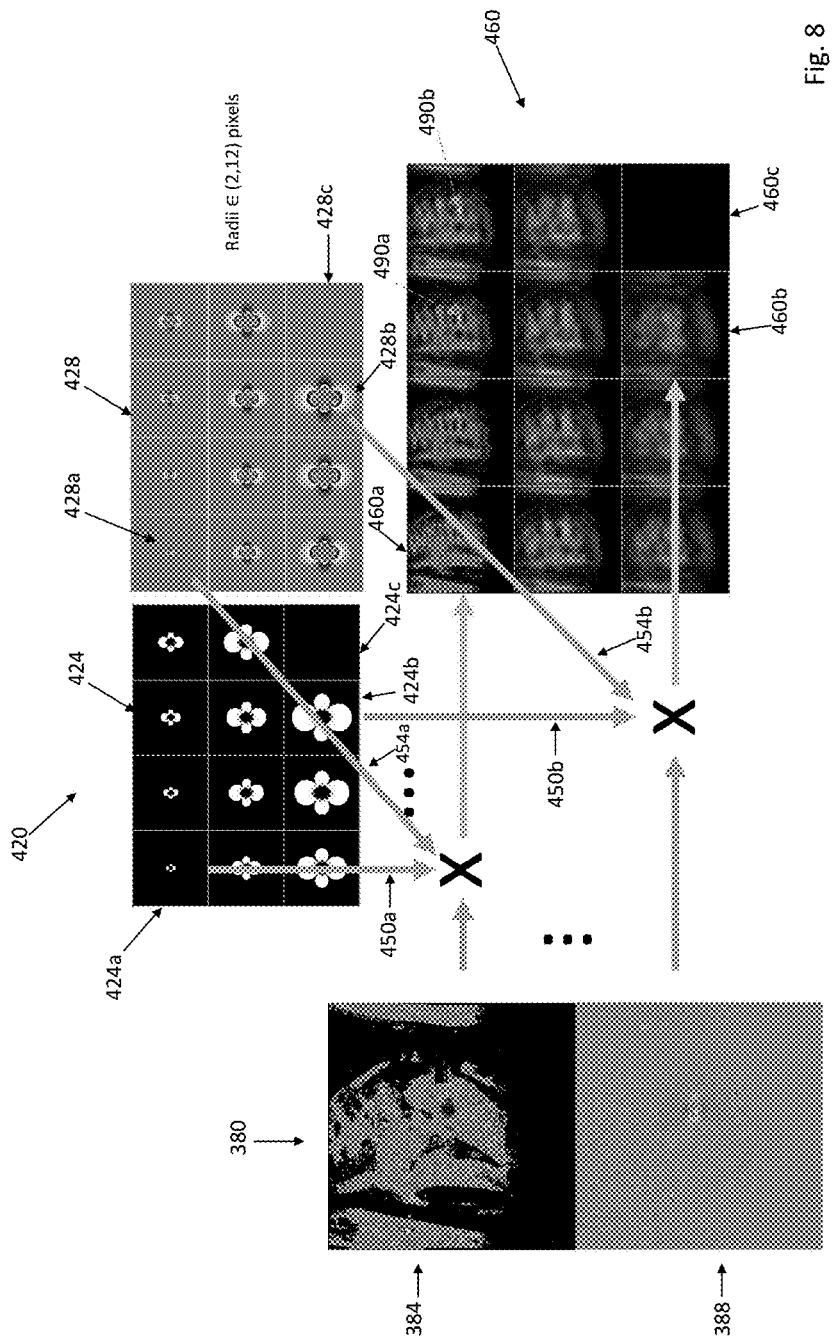
FIG. 8 is a schematic illustration of a comparison method, according to various embodiments.

While FIG. 7 illustrates an example of a magnitude comparison image 384 and a phase comparison image 388, the bubble image library that is accessed in block 194 may be compared to the comparison image data 380 to assist in determining and/or to automatically identify a bubble, if one is present in the comparison image data. Turning reference to FIG. 8 the comparison image data 380 may include the magnitude comparison image 384 and the phase comparison image 388. The comparison image data 380 may be compared to the accessed bubble library in block 220, as illustrated in FIG. 4. As schematically illustrated in FIG. 8, a bubble image library 420 is illustrated. The bubble image library 420 may include a plurality or array of magnitude bubble model 424 and an array or plurality of phase bubble models 428.

In the bubble image library 420, the array of magnitude bubble images 424 may include selected number of bubbles, such as including a range between a bubble having a two voxel radius in a first block 424a and a bubble having a twelve voxel radius in cell 424b. It is understood that a no bubble cell (e.g. no phase difference) 424c may also be present in the library 420.

Similarly, the phase bubble image library 420 may also include phase bubble images for a plurality of diameters including a two voxel diameter cell 428a, a twelve voxel diameter cell 428b, and a no bubble cell 428c. As discussed above, the bubble image library 420 may also include a plurality of bubble images for bubbles rotated relative to the image axis $B_0$. Accordingly, the bubble image library 420, as exemplary illustrated in FIG. 8, is merely exemplary of the plurality of bubble images that may be accessed in the bubble image library in block 194.

Regardless of the number of bubble images accessed in the library 194, which may be compared, either a selected number or sub-plurality of all of the bubble images from the bubble image library may be compared in block 220. As illustrated in FIG. 8, each of the bubble images from the library 420 may be compared to the magnitude comparison image 384 as illustrated by comparison lines 450a and 450b.

As illustrated in FIG. 8, the magnitude image comparison may be made to the magnitude comparison image 384 and may allow for the generation of a correlation image data set or array 460. The correlation array 460 may include representation of a correlation between each of the images in the bubble image library 420 to the comparison image data set 380. Accordingly, the correlation image array 460 may also include correlation regarding the phase bubble images, as illustrated by the comparison lines 454a and 454b. The comparison lines illustrate the first and last bubble image being compared to the comparison image data set 380. Accordingly, the correlation array 460 may include the same number of cells as the bubble image library, where each cell represents a comparison of the respective cell in the bubble image library. The first cell 460a includes a correlation of the first magnitude cell 424a to the comparison magnitude image 384 and the first phase library cell 428a to the comparison phase image 388. The correlation array 460 that includes cells relating to each of the library images, such as including a largest radius correlation cell 460b and a no bubble cell 460c. Accordingly, the correlation array 460 may include correlation between all of the bubble images to the comparison image data 380.

The bubble image library 420 may include the bubble images of bubbles of selected sizes and/or orientations. Further, the bubble images may be cropped to a selected dimension, such as one or two pixels greater than the bubble model. Accordingly, the dimensionality of the bubble images may be less than the size of the comparison image 380. To perform the comparison, therefore, the bubble image from the bubble image library 420 may be moved in a step wise manner across the comparison image 380.

A correlation between the bubble image from the bubble image library 420 and a portion of the comparison images 380 will cause a high correlation, which may be depicted as a bright pixel or voxel in the correlation image in the correlation image array 460. That is, as illustrated in FIG. 8, each of the bubble images may have a selected geometry or intensity or phase deviation, in the respective bubble images of the bubble image library 420. As the bubble image from the bubble image library 420 is compared to a portion of the comparison image 380, each of the pixels or voxels may include a selected correlation. The correlation may be low or high. A high or large correlation may be indicated as a high intensity or high correlation which may be illustrated in the correlation array 460. Again, it is understood, that the correlation data and the correlation array 460 may be illustrated for use by the user 25 and/or used in the system for identification of the bubble. Nevertheless, high correlations may be identified between the bubble images from the bubble image library 420 and the comparison images 380.

In various embodiments, the bubble images in the bubble image library are masked to the voxels with greater than a 0.1 radian phase shift. This masking assists in localizing correlations between the bubble image library image and the comparison images. In addition, the cross correlations may be normalized by mean squared amplitude of the bubble images from the bubble image library to allow for correlations to be compared between library entries. In various embodiments, the correlation may be a comparison and may occur in the Fourier domain, particularly for complex value inputs of the comparison images.

In various embodiments generation of bubble images in the bubble image library may include non-square voxels, since imaging resolution may be different in different dimensions. Also, bubble rotation may take place before or after synthesis of the bubble image, thus bubble coordinates may rotated before calculating the image, or rotate the image afterward.

The bubble image library may also be processed using a technique such as singular value decomposition or principle component analysis, to reduce its dimension for more efficient computation. In other words, instead of directly calculating correlations between the comparison image and each bubble image library entry, correlations may be determined between the comparison image and a smaller number of optimized linear combinations of bubble image library entries.

The correlation for each of the correlation images in the correlation array 460 may be given a correlation score $S_{ij}$ denoted by Equation 6, $$S_{ij} = \max\left(\frac{|X_{ij}| - |X_{ij}^b|}{1 - |X_{ij}^b|}, 0\right)$$

In Equation 6, the correlation score may be a maximum of a correlation between the bubble image having a selected radius i and angle j, for each of the bubble images from the bubble library. As noted in Equation 6, the correlation score may attempt to remove background noise by providing a correlation $X_{ij}^b$ that is a correlation between each of the bubble images in the bubble image library and a tissue mask. The tissue mask may be based upon an initial image, such as an image prior to any ablation or therapy being applied to the subject 28 and/or an initial heat image. Accordingly, a mask may be used to remove false correlations that may occur in the image. For example, in various embodiments, heat formation in the subject 28 may cause phase change or phase deviation that may confound the bubble detection. Accordingly, masking the image or removing background may assist in achieving a greater bubble detection accuracy. It is understood that the optional tissue mask may also be formed with the immediate previous accessed heat image from block 202. Accordingly, a mask may include image data or a correlation based upon possible heat that cause a phase change over the course of the treatment.

The bubble image library may have the bubble images formed at a selected resolution that may be substantially greater than the resolution of the comparison images. The resolution of the bubble images may be at a resolution great enough to allow for a detailed generation of the bubble images for comparison to the comparison images. Accordingly, during or after the generation of the correlation image array 460, the correlation image array, including the images therein, and/or the comparison images 380, if upscaled, may be low pass filtered with a selected Gaussian function or kernel, such as a normalized Gaussian kernel. The resolution of the comparison image 380 and the correlation image 460 may be reduced to a resolution similar to that of the acquired image data, such as the current heat image from block 194.

After the low pass filter, pixels within the correlation images may be identified as bubble pixels if the pixel or voxel has a magnitude that is below a selected magnitude, if selected. As discussed above, a ratio magnitude of 0.65 may be a selected threshold. Accordingly, if a voxel does not have a signal reduction of at least 35%, it may not be included in a possible bubble detection. In addition, if the signal in a voxel increases rather than decreases, it may not be included in a possible bubble determination. Further, voxels having a selected correlation score of at least 0.2, as discussed above, may also not be included in a bubble detection. The correlation score may have any appropriate value, such as 0.3, 0.4, or higher. A selected higher maximum may reduce a number of voxels selected to possibly be within a bubble. Accordingly, voxels that meet at least these two requirements may be included in a bubble detection. As illustrated in FIG. 8, the correlation images 460 may be used to identify an image or one of the correlation images as having a voxel or group of voxels that are within a bubble as illustrated by 490a and/or 490b. The images that may be included in a bubble may then be confirmed or processed, as discussed further herein.

The comparison and determination of the correlation images or correlations 460 may be executed instructions, such as with the processor system 40. Thus, the correlations 460 may be determined substantially automatically based on the instructions formed based on the disclosed method and process.

Further, as discussed above, the comparison of the bubble images from the bubble image library 420 may be made to the comparison images 380. However, as discussed above, the determination of a bubble may be relevant at or near the instrument 24 within the subject 28. Accordingly, the comparison image 380 may be reduced in dimensionality, such as by identifying a region of interest (ROI) within the comparison image 380 and/or the heat image. In various embodiments, the instrument 24 may be navigated by being tracked with a selected tracking system, as discussed above.

As the current heat image accessed in block 198 may be generated with the imaging system 26, the position of the instrument 24 within the image data may be determined, as discussed above. Thus, the comparison of the bubble images from the bubble image library may be minimized to a selected area or volume around a distal end of the instrument 24 within the subject (such as when the subject is registered to the image), such as the comparison image 380. The amount of the image for comparison to the bubble images may be selected to be only within a selected volume or area relative to the tracked location of the instrument.

In addition or alternatively thereto, the user 25 may also identify a region of interest for comparison to the bubble images from the bubble image library 420. The user 25 may identify the ROI by one or more input devices, such as the keyboard 44. In various embodiments, the user 25 may draw or identify the ROI on the image 23 displayed with the display device 22. Accordingly, an optional area or volume of a region of interest may be identified for a comparison in block 220. The comparison of the bubble image to the generated comparison image may be in either one or both of the whole image and/or a selected region of interest. The region of interest, as noted above, may be based upon selection by the user 25, a tracked location of the instrument 24 such as being tracked with the navigation system, or an inherently registered position of the image relative to the subject 28. For example, the ROI may be within a volume that is about 0.1 cm to about 5 cm from a selected location of the end of the instrument 24. Nevertheless, the comparison of the bubble image may be made to an appropriate portion of the comparison image for determining whether a bubble is present within the image.

Returning reference to FIG. 4, after identifying a location of a bubble in the comparison image, a determination of whether to compensate or not may be made in block 248. If no compensation is determined, as discussed above various steps may be followed, such as pausing therapy to allow the bubble to dissipate. However, if compensation is determined, the YES-path 260 may be followed to the removed distortion/artifact caused by a bubble from the current heat image in block 270.

The compensation may include the removal of the distortion, such as phase variance, caused by a bubble in the heat image and/or the comparison image. In various embodiments, therefore, the compensation may include a subtraction of the bubble image from the bubble image library that most matches the identified bubble. Thus, removing the bubble distortion as the bubble image from the bubble image library that is identified in the generated comparison images may be removed. The bubble image may be removed as being placed on the heat image or the comparison image as a determined center of the identified bubble in the image. In various embodiments, the center may be a weighted mean center in the image. The bubble may be subtracted or removed from the image by removing the information of the bubble image from the bubble image library from the heat image.

Figure 9:
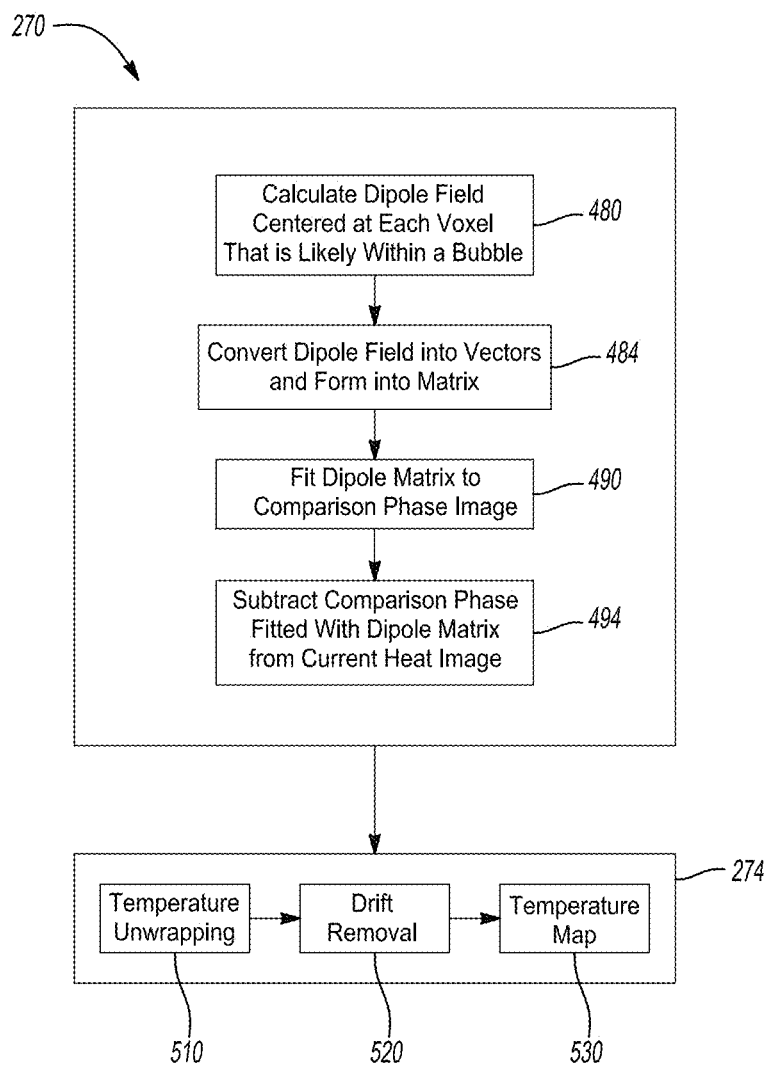
FIG. 9 is a flowchart that details the method of bubble detection and compensation of FIG. 4, according to various embodiments.

In various embodiments, with continuing reference to FIG. 4 and additional reference to FIG. 9, the removed distortion in block 270 is illustrated an alternative and/or greater detail. As noted above, the removed distortion may be identified or determined to be a sub-routine as a part of the method 180. As also noted above, the remove distortion 270 and temperature determination 274 may be executed instructions, such as with the processor system 40. Thus, the distortion removal and compensation may be determined substantially automatically based on the instructions formed based on the disclosed method and process.

Accordingly, with reference to FIG. 9, the removed distortion method or sub-routine is described in greater detail. Once the bubble is identified in block 244, all of the voxels in the comparison image that are part of the bubble and/or likely part of a bubble may be identified. Accordingly, all of the voxels inside of the bubble (i.e. as identified by the bubble image from the bubble image library accessed in block 194) may have a dipole field calculated for each voxel centered at each of the voxels. The dipole field may be generated as a matrix, which may be referred to as matrix A, and be defined by Equation 7, $$\frac{((x-xc)^2 - (y-yc)^2)}{((x-xc)^2 + (y-yc)^2)}$$

Equation 7 is the difference of the squared x and y coordinates in the image divided by their sums. The coordinates are centered at the voxel location identified as xc and yc. Accordingly, the calculation of the dipole field may be made in block 480. The dipole field is a map based upon the x and y locations within the image and may be formed into vectors in block 484. The vectors may be formed into two columns of a matrix. The dipole matrix may then be used to analyze the comparison phase image 388, as discussed above in FIG. 7 and FIG. 8.

The dipole matrix may be fitted to the phase comparison phase image, such as the image 388, in block 490. The fitted phase image may be subtracted from the current heat image in block 494. The subtraction of the comparison phase image 388 that is fitted with the dipole matrix may be used to determine the proper heat or the phase change due to heat within the current heat image that is not affected by the bubble.

The dipole matrix may be used to identify or clarify the voxels in the current heat image that are phase distorted caused by the bubble rather than a phase change due to heating of the tissue within the subject 28. Accordingly, subtracting the comparison phase image fitted with the dipole matrix from the current heat image removes the phase distortion caused by the bubble, rather than heat. Thus, the removed distortion/artifact of the bubble in block 270 may allow for a determination of the temperature in block 274 at all of the voxels within the current heat image 198.

With continuing reference to FIG. 9, and with returning reference to FIG. 4, the determination of the temperature in the current heat image may be based upon the removal of the phase distortion caused by the bubble. Accordingly, once the bubble phase is removed, the temperature may be determined in block 274. Further, with reference to FIG. 9, the temperature determination may include various sub-steps or a sub-routine. For example, temperature determination in block 274 may include a temperature unwrapping in block 510. The temperature unwrapping in block 510 may include correcting for phase wrap when phase encoding the heat determination image accessed in block 198. Accordingly, temperature unwrapping may incur, due to the phase, in block 510.

The temperature determination may also include drift removal in block 520. Drift removal may include determination of a temperature drift over time. Temperature drift over time may occur for various reasons, and drift removal may include determination of a temperature drift over time, such that the accumulation of phase drift is monitored and temperature data are adjusted for this drift artifact across the image anatomy. Accordingly, a summation of all heat images may be made to determine a masking and/or subtraction of heat drift that may have occurred prior to the current heat image accessed in block 194. Other appropriate methods to determine drift and/or for its removal may also be used. For example, a drift correction may be derived from the instantaneous heating image (e.g. the current heat image), by fitting a low order polynomial to the entire phase difference image (e.g. the phase portion of the comparison image (i.e. phase variance image 388, and then subtracting it out of the temperature map that is based on the current heat image.

Finally, a temperature map may be made in block 530 based upon the removal of the bubble phase distortion and accounting for optional additional features such as temperature unwrapping and drift removal in blocks 510, 520, respectively, as discussed above. The temperature map may include a determined temperature for each voxel in the current heat image access in block 198. The temperature determination may also include or be a temperature differential from a previous heat image. Further, as noted above, the determination may be based upon information collected with the image data acquired with the imaging system 26 of the subject 28. In various embodiments, the information may include phase change or other information, such as relaxation times, for each voxel in the image. In various embodiments, the determination of the temperature may be performed according to generally known techniques, such as those used in the Visualase® cooling laser fiber system sold by Medtronic, Inc. The temperature map created in block 530, however, may be made after a removal of a bubble or possible bubble that is identified in the current heat image, according to the method 180, including the various sub-steps as noted above.

Accordingly, the procedure may be performed on a subject and a temperature may be determined with an image, as discussed above. The temperature may be determined regardless of whether the formation of a bubble occurs or not, including or based upon the method as noted above. Thus, a bubble may occur in an image, it may be automatically identified according to instructions executed with a processor based upon the algorithm noted above, and a corrected or undistorted temperature map may be generated based upon the current heat image. Thus the user 25 may determine or have determined the temperature map for the subject.

Returning reference to FIGS. 1 and 2 and with further reference to FIG. 4, at least one bubble image from the accessed bubble image library may be compared to the comparison image in block 220. In comparing the at least one bubble image library, as noted above, all of the images in the image bubble library may be compared to the comparison bubble image. As noted above, each of the bubble images may include selected pixels or voxels (based upon the type of image generated and the comparison image), for allowing for a comparison between the bubble image and the comparison image. Generally, a pair wise comparison between pixels and/or voxels in the bubble image is made with pixels and/or voxels in the comparison image. To compare the bubble image to the entire heat image, however, may include extraneous or superfluous correlations and/or may increase analysis time. In various embodiments, therefore, as noted above, a region of interest (ROI) may be determined for limiting or defining only an area or volume in which the comparison of the bubble image is made to the comparison image. In various embodiments, the ROI may be determined based upon navigating the instruments 24 in the subject 28.

Figure 10:
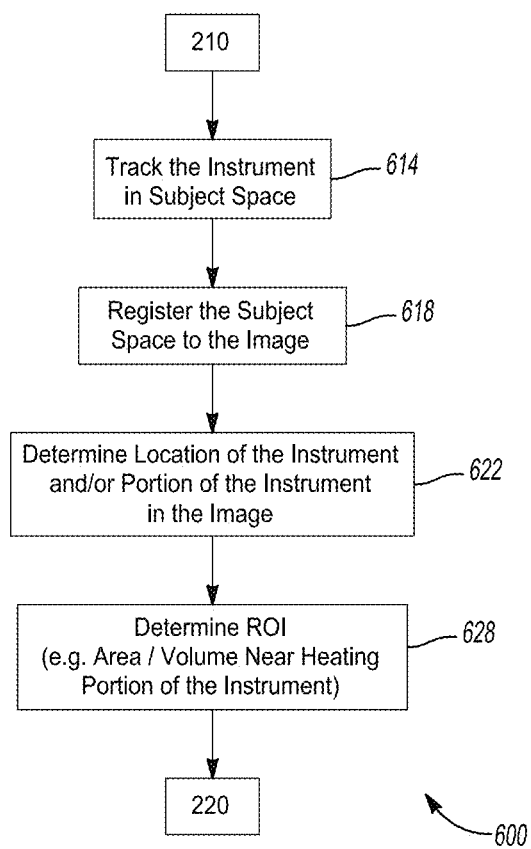
FIG. 10 is a flowchart that details of a method to determine a region of interest, according to various embodiments

With additional reference to FIG. 10, a navigated determined region of interest 600 is illustrated. The navigated determined region of interest may be incorporated into the method 180 illustrated in FIG. 4, such as immediately prior to the compared at least one bubble image from the accessed bubble image library to the current image in block 220. It is further understood that, as illustrated in FIG. 4, the determination of the ROI may be a sub-routine incorporated into the comparison in block 220. Accordingly, the determined ROI 600 may be understood to be a sub-routine incorporated into the method 180. Thus, as noted above, the method 600 may be executed instructions, such as with the processor system 40. Thus, the method 600 may be determined substantially automatically based on the instructions formed based on the disclosed method and process.

Generally, when navigating the instrument 24 during a selected procedure, the instrument 24 may be tracked with a selected tracking system, such as the tracking system 50 discussed above, to determine a location of at least a portion of the instrument 24. Accordingly, the determined ROI method 600 may begin within the method 180 with the comparison block 210 and proceed to track the instrument in block 614.

In tracking the instrument in block 614, a location of the instrument 24 may be determined by the navigation system 20. The location of the instrument 24 may be determined relative to the subject 28, such as with the DRF 58. As noted above, the images of the subject 28, including the image 23, may be registered to the patient 28. In various embodiments, the image 23 may be registered to the subject 28 in block 618. Accordingly, the tracked location of the instrument 24 may be known relative to the image 23 based upon tracking the instrument in block 614. Registration may occur in any appropriate manner, including those discussed above, such as with identifying fiducial points in the subject 28 and the image 23 (fiducials may be natural or implanted artificially). Regardless, the image may be registered in block 618.

Thus, the tracked position of the instrument in block 614 may be determined relative to the image in block 622. In determining the location of the instrument in block 622, a region within the image 23 may be identified in the image space. As noted above, at least a portion of the instrument may have its location determined, such as the terminal end 110 of the instrument 24 and/or the distal end 104 of the energy delivery device 100. The location of the portion of the instrument, such as the terminal end of the fiber optic member or energy delivering device 100, may be used to identify a region relevant for temperature determination.

A determined region of interest may be based upon a determined location of the instrument in block 622 by determining a region of interest in block 628. The determined region of interest may include a selected area or volume around or near the determined location of the instrument or portion of the instrument. For example, a determined region of interest may be defined as a volume having a radius of a selected length (e.g. about 1 cm to about 6 cm and/or about 2 pixels or voxels to about 12 pixels or voxels). The region of interest may be centered on or near the determined location of the portion of the instrument and may be determined in block 628.

In various embodiments, the processor, such as the processor system 40 discussed above, may recall a predetermined or determine a size of a region of interest. It is understood, however, that the user 25 may also define a region of interest relative to the tracked position of the instrument and the determined position of the instrument in block 622. Accordingly, determining the region of interest in block 628 may be identifying the portion of the image 23 (e.g. tracked center of the heating portion of the instrument and a volume in a selected radius therefrom).

As noted above, the determining of the ROI may be a sub-routine of the block 220. As illustrated in FIG. 10, however, the determination of the ROI 600 may be inserted between the generated comparison image in block 210 and the compared at least one bubble image from the accessed bubble image library to the current comparison image in block 220. Accordingly, the determined ROI with the navigation of the instrument 24 may be understood to be inclusive or included, as a selected option, within the method 180.

Returning reference to FIG. 4, as noted above, the comparison to determine portion of an image as to whether a bubble is present or possibly present in an image occurs in the method 180 at block 220. As discussed above, with reference to FIG. 4 and FIG. 5, a bubble image may be generated and/or accessed for comparison to the comparison image. The bubble image may be based upon a model of a bubble and an image of the model bubble, including a magnitude and phase variance. In various embodiments, however, in addition to the bubble image model and/or alternatively thereto, a bubble may be identified and/or a possible bubble may be identified by analysis of the comparison image directly. In various embodiments, a heuristic method may be applied in addition to and/or alternatively to the bubble image model as discussed above.

Figure 11:
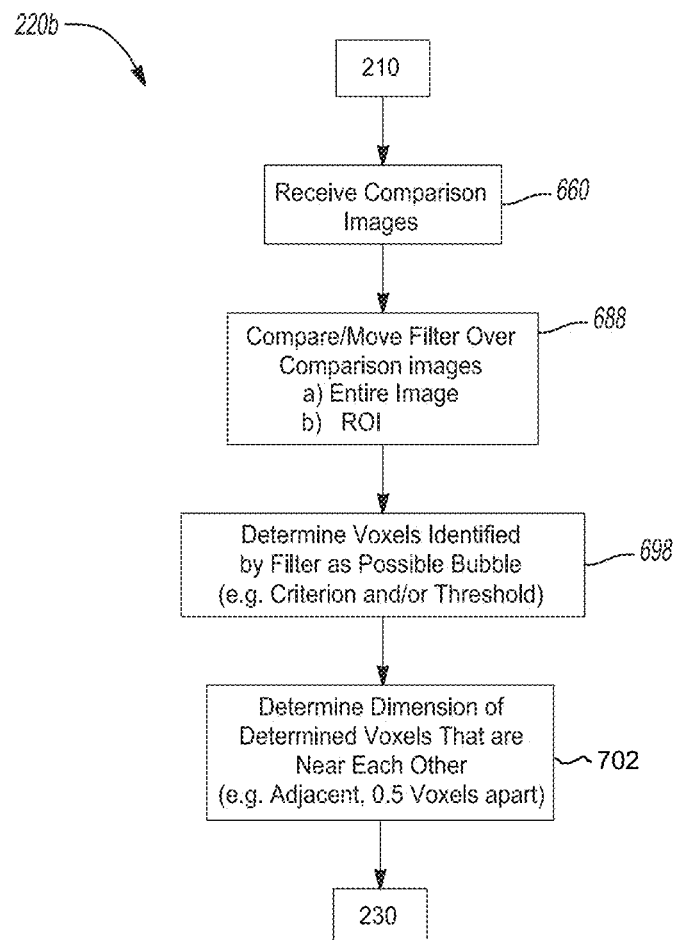
FIG. 11 is a flowchart illustrating a method of determining a bubble in an image, according to various embodiments.

With continuing reference to FIG. 4 and additional reference to FIG. 11, a method 220b is illustrated. The method 220b may be an addition to and/or alternative to the comparison of the bubble image from the bubble image library, as discussed above. The comparison method 220b, however, may be included in the method 180, as illustrated in FIG. 4, to determine whether a bubble is present in block 230 and the identified location of the bubble in the comparison image in block 244. Thus, the comparison method 220b may be included or understood to be a sub-routine within the method 180, as discussed above.

Thus, the bubble image comparison algorithm or system, as discussed above and illustrated in various figures such as FIG. 6 and FIG. 8, may also be an alternative and/or addition to the method 220b. The method illustrated in FIG. 6 and FIG. 8 including the bubble image library may also be understood to be a sub-routine of the method 180.

The heuristic or non-model comparison 220b may begin at block 210, as discussed above. The comparison image may be generated in block 210 and received for comparison in block 660. The received comparison image or images may include the comparison image data 668, as illustrated in FIG. 12. The comparison image data 668 may be similar to the image data 380, as discussed above. Generally, the comparison image data may be a ratio of the current heat image 160 and the prior or previous heat image 150. As discussed above, the current heat image 160 may or may not include one or more voxels or pixels that include a selected or have a selected change when compared to the prior heat image 150. In various embodiments, as discussed above, the comparison image data 668 may be based upon a ratio of the current heat image 160 and the previous heat image 150. As also discussed above, the comparison image data 668 may include a magnitude image data 670 and a phase variance image data 674. As exemplary illustrated in FIG. 12 the magnitude image data 670 may include a region of magnitude change or decrease 678 and the phase variance initiated 674 may include a phase variance region or area 682.

In the comparison method 220b, a filter 692 may be moved over the comparison image in block 688. The filter may be defined and/or saved in a selected memory, such as in the memory 46. The processor system 40 may then recall the filter and compare it or move it over the comparison image data 668, as discussed further herein.

The filter may be defined to attempt to identify or to identify clusters or localized regions of voxels or pixels that include selected criteria or variances. The variances may be predefined and included within the filter stored in the memory 46. In various embodiments, however, the user 25 may also identify selected features or criteria to include in the filter for comparison to the comparison image in block 688.

The filter may include a selected size such as about 2 voxels to about 15 voxels, including about 7 voxels to about 11 voxels, and further including about 9 voxels. The filter may have a selected dimension, therefore, and may be moved within a selected dimension of the comparison image. As discussed above the filter may be moved within the entire image. In various embodiments, however, the filter may also be moved within a region of interest. As noted above, the region of interest may include a manually selected region of interest (e.g. a region of interest identified by the user 25, such as by drawing or identifying with an input a ROI in the image 23) and/or automatically determined based upon selected features, such as within the ROI determination 600 illustrated in FIG. 10. Accordingly, it is understood that the filter may be applied to the comparison image in any appropriate region, including the entire image or only a region of interest which may be less than the entire image.

The filter may be to determine or identify selected voxels within the comparison image 668 that may include or be determined to be within a bubble. The filter, therefore, may be applied to the comparison image data 668 by the processor system 40, in a manner similar to applying the bubble image as discussed above. Thus, the filter may be applied in a substantially pairwise manner relative to the comparison image 668 to determine a comparison and/or determination of whether a voxel meets a selected threshold, as discussed further herein.

The filter 692, as illustrated in FIG. 12 may be illustrated as an area or volume filter 692, as discussed above. In various embodiments, the filter may include or be inclusive of at least two features or criteria, but are illustrated separately in FIG. 12. For example, in the magnitude image 670, the filter 692 may include the selected dimensions, as discussed above, and identify or be compared to the magnitude image 670 to determine a selected signal drop. The selected signal drop may include or be defined as a magnitude change in the ratio or comparison image data 668 of a voxel of at least about 0.5 to about 0.95, and further including about 0.7 to about 0.9, and further including a magnitude variance in the comparison image 668 of about 0.8. In other words, the filter may identify a signal decrease of about 20% from the heat image to the current heat image as slightly being inclusive within a bubble.

The filter 692b may include a second criterion that is compared or moved across the phase variance image 674. The filter may identify in the phase variance image 674 voxels that have a phase variance of about 0.5 radians to about 1.5 radians, further including about 1 radian. The phase variance may be identified or determined on a per-voxel basis, such as in a pair wise comparison between the filter 692b and the voxels in the phase variance image 674.

The filter 692, therefore, is moved over or compared to the comparison image data 668, including either the entire image and/or within a region of interest, as discussed above. Based upon the evaluation of the voxels within the filter, a determination of whether identified voxels are possibly within a bubble is made in block 698. As discussed above, the filter may be used to identify voxels that are possibly within a bubble based upon the selected criteria and/or thresholds noted above, regarding the magnitude and phase variance. All of the voxels identified as possibly within a bubble, based upon the filter 692, may then be determined or saved in block 698. Generally, a voxel may be determined to possibly be within a bubble if the voxel meets both criteria, such as having a magnitude variance of about 0.8 (i.e. signal decrease of about 20%) and a phase variance of about 1 radian.

Once the voxels are determined or identified to be possibly within a bubble in block 698, a dimension of voxels within a selected distance of one another may be made in block 702. As discussed above, the filter 692 may be used to determine whether selected voxels or whether voxels have a selected magnitude change (e.g. signal drop) and/or phase variance. Generally, a voxel determined to be possibly within a bubble will be required to include both thresholds, as discussed above.

A bubble may be determined to have a selected dimension and/or geometry. For example, a bubble may be assumed to have a radius of at least about 2 voxels and/or equal to or less than about 12 voxels. Accordingly, determining a dimension of a cluster of voxels in block 702 may be used to identify whether a bubble is present in the comparison image 668. A cluster may be voxels that meet the bubble filter criteria that are adjacent (e.g. touching) one another or within a selected distance (e.g. 0.5 voxels apart). All voxels that meet the distance criteria may be identified as a cluster. Once the dimension of any cluster of voxels is determined in block 702, a determination of whether a bubble is present in block 230 may be made.

The determination of whether a bubble is present in the comparison image in block 230, based upon the heuristic comparison 220b, may include whether any determined voxels in block 698 meet an identified or selected dimension in block 230 once the cluster has been determined in block 702. Accordingly, if the cluster of voxels has been identified and includes a dimension of at least 2 voxels, a determination that a bubble is present in the comparison image may be made in block 230. Accordingly the YES-path 238 may be followed, as illustrated and discussed in FIG. 4 above.

If no cluster or no cluster of voxels is not determined to meet a size criterion, such as less than 2 voxels and/or greater than 12 voxels, determination that a bubble is not present in the image may be made in determination block 230 and the NO-path 234 may be followed. It is understood that the dimension of a cluster may be predetermined, and included in the filter, for analysis by the processor system 40. It is also understood that the user 25 may also input a selected cluster dimension for analysis of the comparison image 668. Accordingly, the comparison method 220b may be used to compare and/or assist in identifying or determining whether a bubble is present in the comparison image. Either alone and/or in combination to the comparison with the bubble image library image, as discussed above.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A method of selecting a region for determining a presence of a bubble in an image, comprising:
    tracking a location of at least a portion of an instrument positioned within a subject in a subject space defined by the subject;
    accessing a current image of the subject having an image space that is registered to the subject space;
    determining a location of the instrument within the image space based on the tracked location of the instrument and the accessed current image;
    determining a region of interest in the accessed current image and image space based at least on the determined location of the instrument within the image space;
    analyzing image data of the current image with at least a bubble image library to determine if a bubble is present in the current image within the region of interest;
    identifying image portions of the analyzed current image that include the bubble;
    generating a comparison image by removing the identified image portions in the current image that include the bubble; and
    outputting feedback to a user in light of the comparison image regarding continuing with a procedure performed by the instrument.

2. The method of claim 1, further comprising:
    tracking the instrument within the subject space with a tracking system, the location of the instrument is a tracked location; and
    registering an image space of the current image to the subject space of the subject;
    wherein the location of the instrument within the image space is determined based on the tracked location of the instrument.

3. The method of claim 2, further comprising:
    operating the tracking system to determine the tracked location separate from the imaging system.

4. The method of claim 1, wherein analyzing the image data of the current image to determine if the bubble is present in the current image within the region of interest, comprises:
    comparing at least one bubble image to the current image;
    determining a correlation between the at least one bubble image and the current image; and
    outputting a correlation value based on the determined correlation.

5. The method of claim 4, further comprising:
    accessing the bubble image library including a plurality of bubble images.

6. The method of claim 4, wherein analyzing the image data of the current image to determine if the bubble is present in the current image within the region of interest, further comprises:
    selecting a first region within the region of interest;
    performing a pairwise comparison of voxels from the at least one bubble image to the selected first region;
    selecting a second region within the region of interest; and
    performing a pairwise comparison of voxels from the at least one bubble image to the selected second region.

7. The method of claim 1, wherein tracking the location of at least the portion of the instrument positioned within the subject in the subject space defined by the subject, comprises:
    associating a tracking device with the instrument; and
    operating a tracking system to track the tracking device associated with the instrument.

8. The method of claim 1, wherein determining the region of interest relative to the determined location of the instrument within the image space, comprises:
    determining a dimension of the region of interest; and
    centering the region of interest on the location of the instrument.

9. The method of claim 8, wherein the location of the instrument includes the location of only a portion of the instrument.

10. A system to select a region for determining a presence of a bubble in an image, comprising:
    a navigation system operable to:
        determine a location of an instrument positioned within a subject in a subject space defined by the subject,
        access a current image of the subject having an image space that is registered to the subject space, and
        determine a location of the instrument within an image space; and
    an image analysis processor system operable to execute instructions to:
        identify a region of interest relative to the determined location of the instrument within the image space, analyze image data of the current image with at least a bubble image library to determine if a bubble is present in the current image within the region of interest, identify image portions of the analyzed current image that include the bubble, generating a comparison image by removing the identified image portions in the current image that include including the bubble, and output feedback to a user in light of the comparison image regarding continuing with a procedure performed by the instrument.

11. The system of claim 10, further comprising:
a display device to display a heat map image of the subject based on the current image.

12. The system of claim 11, further comprising:
a memory system having stored thereon the bubble image library including a plurality of bubble images;
wherein the image analysis processor system is operable to recall the bubble image library.

13. The system of claim 12, wherein the image analysis processor system is operable to execute further instructions to analyze the current image to determine if the bubble is present in the current image within the region of interest by:
comparing at least one bubble image recalled from the bubble image library to the current image;
determining a correlation between the at least one bubble image and the current image; and
outputting a correlation value based on the determined correlation.

14. The system of claim 10, wherein the image analysis processor system is operable to execute further instructions to identify the region of interest by determining a region centered on the determined location of the instrument within the image space.

15. A method of selecting a region for determining a presence of a bubble in an image, comprising:
accessing a first image and a second image of a subject in which an instrument is positioned;
generating a first comparison image by comparing the first image and the second image;
determining a location of the instrument within an image space of at least the comparison image based on a determined location of the instrument;
determining a region of interest relative to the determined location of the instrument within the image space;
correcting at least the second image for determining a temperature of at least the region of interest in the second image;
identifying image portions of the comparison image including the bubble;
generating a second comparison image by removing the identified image portions of the first comparison image including the bubble; and
outputting feedback to a user in light of the second comparison image regarding continuing with a procedure performed by the instrument.

16. The method of claim 15, further comprising:
tracking the instrument in a subject space defined by the subject; and
registering an image space of the second comparison image to the subject space of the subject.

17. The method of claim 16, further comprising:
comparing a plurality of bubble images to the first comparison image;
determining a correlation between at least one bubble image of the plurality of bubble images and the first comparison image; and
outputting a correlation value based on the determined correlation of the at least one bubble image.

* * * * *

UNITED STATES PATENT AND TRADEMARK OFFICE
CERTIFICATE OF CORRECTION

PATENT NO. : 11,896,288 B2
APPLICATION NO. : 17/879823
DATED : February 13, 2024
INVENTOR(S) : Christine R. Drown et al.

Page 1 of 1

It is certified that error appears in the above-identified patent and that said Letters Patent is hereby corrected as shown below:

In the Specification

Column 6, Detailed Description, Line 37, Delete "alterative" and insert --alternative-- therefor Column 7, Detailed Description, Line 49, Delete "110" and insert --104-- therefor Column 7, Detailed Description, Line 56, Delete "24$i$'" and insert --24$i$-- therefor Column 13, Detailed Description, Line 26, Delete "$\Delta$ f." and insert --$\Delta$f.-- therefor Signed and Sealed this
Twelfth Day of November, 2024

Katherine Kelly Vidal
*Director of the United States Patent and Trademark Office*